US011466326B2

(12) United States Patent
Sun

(10) Patent No.: US 11,466,326 B2
(45) Date of Patent: Oct. 11, 2022

(54) METHODS AND KIT FOR DIAGNOSING AND TREATING COLORECTAL CANCER BASED ON AVRA AND WNT1

(71) Applicant: The Board of Trustees of the University of Illinois, Urbana, IL (US)

(72) Inventor: Jun Sun, Chicago, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 453 days.

(21) Appl. No.: 16/456,555

(22) Filed: Jun. 28, 2019

(65) Prior Publication Data

US 2020/0010895 A1 Jan. 9, 2020

Related U.S. Application Data

(60) Provisional application No. 62/694,168, filed on Jul. 5, 2018.

(51) Int. Cl.
*C12Q 1/6883* (2018.01)
*G01N 33/569* (2006.01)
*G01N 33/574* (2006.01)

(52) U.S. Cl.
CPC ..... *C12Q 1/6883* (2013.01); *G01N 33/56916* (2013.01); *G01N 33/57419* (2013.01); *C12Q 2600/158* (2013.01); *G01N 2333/255* (2013.01)

(58) Field of Classification Search
None
See application file for complete search history.

(56) References Cited

U.S. PATENT DOCUMENTS

| | | | | |
|---|---|---|---|---|
| 4,208,479 | A * | 6/1980 | Zuk | C07J 41/0016 435/7.9 |
| 2011/0178030 | A1* | 7/2011 | Sun | A61P 29/00 514/21.2 |
| 2012/0012472 | A1 | 1/2012 | Ahrens et al. | |
| 2012/0039798 | A1 | 2/2012 | Sun | |
| 2016/0022767 | A1 | 1/2016 | Neish et al. | |

FOREIGN PATENT DOCUMENTS

EP 2296683 A2 3/2011

OTHER PUBLICATIONS

Janeway et al., Immunobiology: the Immune System in Health and Disease (1999), Elsevier Science Ltd/Garland Publishing, New York, NY, Fourth Edition, pp. 86-88 (Year: 1999).*
Almagro et al. "Humanization of Antibodies", Frontiers in Bioscience 13, 1619-1633, (2008) (Year: 2008).*
Goel et al., "Plasticity within the Antigen Combining Site May Manifest as Molecular Mimicry in the Humoral Immune Response", The Journal of Immunology 173(12)7358-7367, (2004) (Year: 2004).*
Edwards et al., "The remarkable flexibility of the human antibody repertoire; isolation of over one thousand different antibodies to a single protein, BLyS" J. Mol. Biol. (2003) 334, 103-118, DOI: 10.1016/j.jmb.2003.09.054 (Year: 2003).*
Lloyd et al.,"Modelling the human immune response: performance of a 10e11 human antibody repertoire against a broad panel of therapeutically relevant antigens", Protein Engineering, Design and Selection, vol. 22, Issue 3, Mar. 1, 2009, pp. 159-168, https://doi.org/10.1093/protein/gzn058 (Year: 2009).*
Brown et al., "Tolerance of single, but not multiple, amino acid replacements in antibody VH CDR2: a means of minimizing B cell wastage from somatic hypermutation?", J Immunol. May 1996; 156(9):3285-91 (Year: 1996).*
Vajdos et al., "Comprehensive functional maps of the antigen-binding site of an anti-ErbB2 antibody obtained with shotgun scanning mutagenesis" J Mol Biol. Jul. 5, 2002;320(2):415-28, DOI: 10.1016/S0022-2836(02)00264-4 (Year: 2002).*
Lu et al., Presence of Salmonella AvrA in colorectal tumor and its precursor lesions in mouse intestine and human specimens, Oncotart, 8(33), (2017), p. 55104-55115 (Year: 2017).*
Wang et al., Novel Regulatory Roles of Wnt1 in Infection-Associated Colorectal Cancer, Neoplasia, 20(5), (2018), p. 499-509 (Year: 2018).*
Gradel, et al. (2009) "Increased Short- and Long-Term Risk of Inflammatory Bowel Disease After *Salmonella* or Campylobacter Gastroenteritis." Gastroenterology 137(2)1495-501.
Kato, et al. (2013) "Partial Associations of Dietary Iron, Smoking and Intestinal Bacteria with Colorectal Cancer Risk." Nutr. Cancer 65(2)1169-77.
Lu, et al. (2010) "Chronic Effects of a Salmonella Type III Secretion Effector Protein AvrA In Vivo " PLoS ONE. 5(5): e10505.
Lu, et al. (2012) "Consistent activation of the β-catenin pathway by Salmonella type-three secretion effector protein AvrA in chronically infected intestine." Am. J. Physiol. Gastrointest. Liver Physiol. 303(10):G1113-25.
Lu, et al. (2014) "Enteric bacterial protein AvrA promotes colonic tumorigenesis and activates colonic beta-catenin signaling pathway." Oncogenesis 3:e105.
Lu, et al. (2016) "*Salmonella* Protein AvrA Activates the STAT3 Signaling Pathway in Colon Cancer" Neoplasia 18 (5):307-16.
Sun, et al. (2004) "Bacterial activation of P-catenin signaling in human epithelia." Am J. Physiol Gastrointest. Liver Physiol. 287(1 ):G220-7.
Ye, et al. (2007) "*Salmonella* Effector AvrA Regulation of Colonic Epithelial Cell Inflammation by Deubiquitination." Am J. Pathol. 171(3)1882-92.

* cited by examiner

*Primary Examiner* — Ellen J Marcsisin
(74) *Attorney, Agent, or Firm* — Licata & Tyrrell P.C.

(57) ABSTRACT

A method for identifying a subject having at least an indication or predisposition for developing inflammatory bowel disease or colorectal cancer based upon the presence of *Salmonella* AvrA protein, nucleic acids and antibodies is provided as is a method for treating *Salmonella* infection-related colorectal cancer using a Wnt1 agonist.

1 Claim, 3 Drawing Sheets

Specification includes a Sequence Listing.

METHODS AND KIT FOR DIAGNOSING AND TREATING COLORECTAL CANCER BASED ON AVRA AND WNT1

INTRODUCTION

This application claims benefit of priority to U.S. Provisional Patent Application Ser. No. 62/694,168, filed Jul. 5, 2018, the content of which is incorporated herein by reference in its entirety.

This invention was made with government support under grant numbers DK105118 and DK114126 awarded by the National Institutes of Health. The government has certain rights in the invention.

BACKGROUND

The gastrointestinal tract is a natural habitat for a dynamic and highly competitive microbial community, which is in constant contact with intestinal epithelial cells. Although growing evidence suggests a potential role of microbes in the development of colorectal cancer (Joossens, et al. (2011) *Gut* 60(5):631-7; Marchesi, et al. (2011) *PLoS ONE* 6(5): e20447), evidence to support a direct link of intestinal bacteria to human sporadic colorectal cancer is still limited.

*Salmonella enterica* is a Gram-negative, facultative anaerobe and an intracellular pathogen to both humans and animals, posing a major public health concern worldwide. It is estimated that more than 1 million people in the United States acquire *Salmonella* infection annually as a foodborne illness (Cianflone (2008) *Curr. Gastroenterol. Rep.* 10(4): 424-31). Seroepidemiologic studies have revealed that nontyphoid *Salmonella* infection is much higher (~600 times) what is actually reported (Kuhn, et al. (2012) *J. Med. Microbiol.* 61(Pt 1):1-7), ranging from 56 per 1000 person-years in Finland to 547 in Poland. However, evidence directly supporting an association between *Salmonella* infection and colorectal cancer in human subjects is not well-established.

A common aspect of infection-related cancer is the induction of chronic inflammation, which may promote DNA damage, cell proliferation and migration, through various mechanisms including epigenetic modifications. Many pathogens, such as *Salmonella*, use a type three secretion system (T3SS) to inject numerous virulence factors that induce strong proinflammatory reactions. Whereas most bacteria induce inflammation in the host, some pathogenic bacteria have also evolved the ability to temperate the inflammatory response to create a suitable niche for their survival and proliferation in the host.

AvrA, a T3SS effector protein from *Salmonella enterica*, plays a crucial role in establishing chronic infection (Jones, et al. (2008) *Cell Host Microbe* 3(4):233-44; Ye, et al. (2007) *Am. J. Pathol.* 171(3):882-92; Wu, et al. (2012) *Cell. Microbiol.* 14(1):28-39). AvrA is a 33 kDa protein and a close homologue to a family of acetyltransferases expressed in several enteric pathogens, including YopJ/P in *Yersinia pseudotuberculosis* and VopA in *Vibro parahemalyticus* (Wu, et al. (2012) *Cell. Microbiol.* 14(1):28-39). AvrA exerts anti-inflammatory activities through inhibition of NF-κB and JNK pathways, resulting in reduced secretion of inflammatory mediators (Liu, et al. (2010) *PLoS ONE* 5(t)P: e10505). Furthermore, this JNK inhibition leads to suppression of apoptosis particularly in the context of proinflammatory enteropathogenic Salmonellosis (Jones, et al. (2008) *Cell Host Microbe* 3(4):233-44; Ye, et al. (2007) *Am. J. Pathol.* 171(3):882-92; Wu, et al. (2012) *Cell. Microbiol.* 14(1):28-39), and thus to prolonged bacterial intracellular survival.

It has been reported that antibody against *Salmonella* flagellin is higher in colorectal cancer and pre-cancer cases than in controls in two distinct populations in United States and the Netherlands and that smoking and dietary intake (i.e., iron) is one of the mediating factors, suggesting a possible link of *Salmonella* to colorectal cancer (Kato, et al. (2013) *Nutr. Cancer* 65(2):169-77). Yet, information is still limited regarding frequencies of sustained *Salmonella* infection after initial acquisition in the population. Further, it is not clear how AvrA plays its role in the human colon cancer.

SUMMARY OF THE INVENTION

This invention provides a method of identifying a subject having at least an indication or predisposition for developing inflammatory bowel disease or colorectal cancer comprising detecting in a blood or fecal sample from a subject, the subject having had a previous *Salmonella* infection, the presence of *Salmonella* AvrA protein, nucleic acids encoding *Salmonella* AvrA protein, or an anti-AvrA antibody, wherein the presence of the *Salmonella* AvrA protein, nucleic acids encoding *Salmonella* AvrA protein, or an anti-AvrA antibody identifies the subject as having at least an indication or predisposition for developing inflammatory bowel disease or colorectal cancer. In one embodiment, the presence of *Salmonella* AvrA protein is detected with an anti-AvrA antibody, e.g., an antibody that specifically binds to amino acid residues CGEEPFLPSDKADRY (SEQ ID NO:30) of AvrA protein. In another embodiment, the presence of nucleic acids encoding *Salmonella* AvrA protein is detected by polymerase chain reaction using a set of primers having the nucleotide sequences of GAATGGAAGGCGTT-GAATCTGC (SEQ ID NO:5) and GTTGTGCGCCTT-GAGTATGTTTGTAA (SEQ ID NO:6). In a further embodiment, the presence of the anti-AvrA antibody is detected in an enzyme immunoassay using a multiwell plate, wherein wells of the multiwell plate are coated with purified AvrA protein. As an alternative feature, the method further includes detecting the expression of Wnt1 n colorectal epithelial cells of the subject, e.g., in a polymerase chain reaction using a set of primers having the nucleotide sequences of GAGCCACGAGTTTGGATGTT (SEQ ID NO:14) and TGAGGAGAGAAGAGGGACCA (SEQ ID NO:15).

This invention also provides a kit including at least one of: (i) an antibody that specifically binds to amino acid residues CGEEPFLPSDKADRY (SEQ ID NO:30) of AvrA protein; (ii) a set of primers having the nucleotide sequences of GAATGGAAGGCGTTGAATCTGC (SEQ ID NO:5) and GTTGTGCGCCTTGAGTATGTTTGTAA (SEQ ID NO:6); or (iii) a multiwell plate, wherein wells of the multiwell plate are coated with purified AvrA protein. Optionally, the kit may further include a set of primers having the nucleotide sequences of GAGCCACGAGTTTGGATGTT (SEQ ID NO:14) and TGAGGAGAGAAGAGGGACCA (SEQ ID NO:15).

A method of treating colorectal cancer in a subject is further provided, wherein an effective amount of an agent that increases Wnt1 expression or activity is administered to a subject having had a previous *Salmonella* infection thereby treating the subject's colorectal cancer.

DETAILED DESCRIPTION OF THE INVENTION

Figure 1:
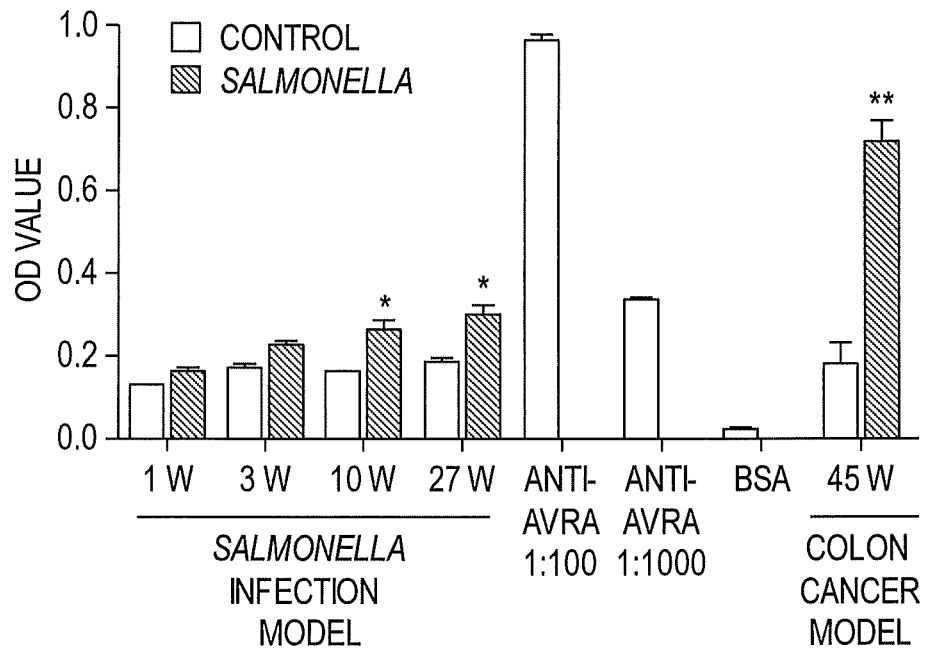
FIG. 1 shows ELISA measurements of anti-AvrA protein in mouse serum. In a *Salmonella* infection model and colon cancer model, mice were infected with *Salmonella* mutant strains Phop$^c$AvrA$^-$/AvrA$^+$ by oral gavage. Serum anti-AvrA were measured at 1, 3, 10 and 27 weeks (W) post-infection in the *Salmonella* infection model and at 45 weeks post-*Salmonella* infection in the colon cancer model. Anti-AvrA antibody was used as a positive control and 1% BSA as a negative control. *P<0.05, **P<0.01, n=3, by Student's t-test.

It has now been found that AvrA is present in inflamed, colorectal tumors and human clinical specimens. Further, anti-*Salmonella* AvrA antibody was found to be present in chronic infected mouse serum samples and human fecal samples. Furthermore, the presence of AvrA protein in inflammatory bowel disease and colorectal tumor tissue in human clinical samples was demonstrated. Moreover, nucleic acids encoding *Salmonella* AvrA were found to be present in human fecal samples. As such, AvrA is of particular use as a marker for identifying an enhanced risk of developing inflammatory bowel disease or colorectal cancer in subjects who have had a previous *Salmonella* infection. In addition to AvrA, it has now been shown that *Salmonella* infection reduces Wnt1 protein expression in intestinal epithelial cells both in vitro and in vivo, wherein said reduction promotes cancer cell migration and invasion. Accordingly, Wnt1 is also of use as a marker for diagnosing colorectal cancer and as a target for the treatment of colorectal cancer in a subject having a previous *Salmonella* infection.

Accordingly, this invention provides a method for identifying a subject having at least an indication or predisposition for developing inflammatory bowel disease or colorectal cancer by detecting the presence of AvrA protein or nucleic acids and/or antibodies of the same, as well as a method for treating colorectal cancer by increasing the expression or activity of Wnt1.

For the purposes of this invention, a "marker" is a gene or protein whose presence in a tissue or cell is associated with, or an indication or predisposition for a disease state. In certain embodiments, AvrA is a surrogate marker for inflammatory bowel disease or colorectal cancer. As used herein, a "surrogate marker" is a marker which correlates with the absence or presence of a disease or disorder, or with the initiation or progression of a disease or disorder. The presence or quantity of such markers is independent of the disease. Surrogate markers are of particular use when the presence or extent of a disease state or disorder is difficult to assess through standard methodologies, or when an assessment of disease progression is desired before a clinical endpoint is reached.

Biologicals samples of particular use in this invention include serum, blood, or fecal samples from a subject that has previously had a *Salmonella* infection. A "subject having had a previous *Salmonella* infection" includes any human, livestock or companion animal that no longer tests positive for a *Salmonella* infection in standard clinical tests, but at some time in the past (e.g., the past 1 month, 2 month, 3 months, 4 months, 6 months, 10 months, 12 months, 2 years, 3 years, 5 years, or years) had a *Salmonella* infection including, but not limited to, *Salmonella* enterica, e.g., serovar Enteritidis or serotype Typhimurium.

In one aspect of the diagnostic method of the invention, the presence of AvrA protein is detected. An "AvrA protein" encompasses AvrA protein and fragments thereof; variant AvrA protein and fragments thereof; peptides and polypeptides including at least a 15 amino acid segment of an AvrA marker or variant marker protein; and fusion proteins including an AvrA marker or variant marker protein. In accordance with this aspect of the invention, an AvrA marker protein is preferably detected in assays using a binding agent which specifically binds to the AvrA marker protein and no other proteins in biological sample being tested.

In assays for detecting the presence of the AvrA protein, a sample is contacted with a binding agent (e.g., an antibody) that specifically binds AvrA protein, and the resulting AvrA protein-binding agent complex is detected using standard assays (e.g., an immunoassay). When the binding agent is, for example, a peptide aptamer, the AvrA protein-binding agent complex can be directly detected by, for example, a detectable marker protein (e.g., β-galactosidase, GFP or luciferase) fused to the aptamer. Subsequently, the presence or absence of the AvrA protein-binding agent complex is correlated with the indication or predisposition for developing inflammatory bowel disease or colorectal cancer.

Binding agents for use in this invention include antibodies, as well as peptide aptamers. Antibodies to AvrA protein can be generated using methods that are well-known in the art. Such antibodies can include, but are not be limited to, polyclonal, monoclonal, chimeric, single chain, Fab fragments, bispecific scFv fragments, Fd fragments and fragments produced by a Fab expression library. For the production of antibodies, various hosts including goats, rabbits, rats, mice, humans, and others, may be immunized by injection with AvrA protein or any fragment or oligopeptide thereof which has antigenic or immunogenic properties. Depending on the host species, various adjuvants can be used to increase the immunological response. Such adjuvants include, but are not limited to, Freund's, mineral gels such as aluminum hydroxide, and surface-active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are particularly suitable.

An antibody to AvrA protein can be generated by immunizing an animal with an oligopeptide, peptide, or fragment of the AvrA protein. Generally, such oligopeptides, peptides, or fragments have an amino acid sequence consisting of at least five amino acids and more desirably at least 10 amino acids. Fragments of the AvrA protein can be generated by, for example, tryptic digestion and extraction from a preparative SDS-PAGE gel or by recombinant fragment expression and purification. Further, short stretches of amino acids of the AvrA protein can be fused with those of another protein such as keyhole limpet hemocyanin and antibody produced against the chimeric molecule. An exemplary antibody is disclosed herein, which was generated by immunization with the 15 amino acid residue peptide CGEEPFLPSDKADRY (SEQ ID NO:30) of AvrA (SEQ ID NO:31; see also GENBANK accession No. AAL21745).

Monoclonal antibodies to the AvrA protein can be prepared using any technique which provides for the production of antibody molecules by continuous cell lines in culture. These include, but are not limited to, the hybridoma technique, the human B-cell hybridoma technique, and the EBV-hybridoma technique (Kohler, et al. (1975) *Nature* 256:495-497; Kozbor, et al. (1985) *J. Immunol. Methods* 81:31-42; Cote, et al. (1983) *Proc. Natl. Acad. Sci.* 80:2026-2030; Cole, et al. (1984) *Mol. Cell Biol.* 62:109-120).

In addition, techniques developed for the production of humanized and chimeric antibodies, the splicing of mouse antibody genes to human antibody genes to obtain a molecule with appropriate antigen specificity and biological activity, can be used (Morrison, et al. (1984) *Proc. Natl. Acad. Sci.* 81:6851-6855; Neuberger, et al. (1984) *Nature* 312:604-608; Takeda, et al. (1985) *Nature* 314:452-454). Alternatively, techniques described for the production of single chain antibodies can be adapted, using methods known in the art, to produce specific single chain antibodies. Antibodies with related specificity, but of distinct idiotypic composition, can be generated by chain shuffling from random combinatorial immunoglobulin libraries (Burton (1991) *Proc. Natl. Acad. Sci.* 88:11120-11123).

Antibodies can also be produced by inducing in vivo production in the lymphocyte population or by screening immunoglobulin libraries or panels of highly specific binding reagents as is well-known in the art (Orlandi, et al. (1989) *Proc. Natl. Acad. Sci.* 86: 3833-3837; Winter, et al. (1991) *Nature* 349:293-299).

Antibody fragments, which contain specific binding sites for the AvrA protein, or a fragment thereof, can also be generated. For example, such fragments include, but are not limited to, the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries can be constructed to allow rapid and easy identification of monoclonal Fab fragments with the desired specificity (Huse, et al. (1989) *Science* 254:1275-1281).

Diabodies are also contemplated. A diabody refers to an engineered antibody construct prepared by isolating the binding domains (both heavy and light chain) of a binding antibody, and supplying a linking moiety which joins or operably links the heavy and light chains on the same polypeptide chain thereby preserving the binding function (see, Holliger et al. (1993) *Proc. Natl. Acad. Sci. USA* 90:6444; Poljak (1994) *Structure* 2:1121-1123). This forms, in essence, a radically abbreviated antibody, having only the variable domain necessary for binding the antigen. By using a linker that is too short to allow pairing between the two domains on the same chain, the domains are forced to pair with the complementary domains of another chain and create two antigen-binding sites. These dimeric antibody fragments, or diabodies, are bivalent and bispecific. It should be clear that any method to generate diabodies, as for example described by Holliger, et al. (1993) supra, Poljak (1994) supra, Zhu, et al. (1996) *Biotechnology* 14:192-196, and U.S. Pat. No. 6,492,123, can be used.

Various immunoassays can be used for screening to identify antibodies, or fragments thereof, having the desired specificity for the AvrA protein. Numerous protocols for competitive binding (e.g., ELISA), latex agglutination assays, immunoradiometric assays, and kinetics (e.g., BIACORE™ analysis) using either polyclonal or monoclonal antibodies, or fragments thereof, are well-known in the art. Such immunoassays typically involve the measurement of complex formation between a specific antibody and its cognate antigen. A two-site, monoclonal-based immunoassay utilizing monoclonal antibodies reactive to two non-interfering epitopes is suitable, but a competitive binding assay can also be employed. Such assays can also be used in the detection of AvrA protein in a sample.

Peptide aptamers which specifically bind to the AvrA protein can be rationally designed or screened for in a library of aptamers (e.g., provided by Aptanomics SA, Lyon, France). In general, peptide aptamers are synthetic recognition molecules whose design is based on the structure of antibodies. Peptide aptamers are composed of a variable peptide loop attached at both ends to a protein scaffold. This double structural constraint greatly increases the binding affinity of the peptide aptamer to levels comparable to that of an antibody (nanomolar range). Likewise, aptamers which bind to nucleic acid molecules encoding AvrA protein, can also be identified in library screens.

Anti-AvrA antibodies can also be obtained from commercial sources. For example, an anti-AvrA antibody developed against amino acid residues 160-259 is available from Creative Diagnostics (Shirley, N.Y.).

A binding agent can also be subjected to other biological activity assays, e.g., cancer cell growth assays, in order to evaluate its potency or pharmacological activity and potential efficacy as a therapeutic agent. Such assays are well-known in the art.

In an alternate embodiment of the diagnostic method of the present invention, the presence of the AvrA protein in a sample is detected via the presence of nucleic acids encoding AvrA protein. Nucleic acids encoding AvrA protein can be detected using any well-known method including, but not limited to, northern blot analysis, reverse-transcriptase PCR, PCR, microarray, and the like. Due to the ease of use, it is generally desirable to detect nucleic acids using a PCR-based approach. In general, this involves contacting the sample with two or more PCR primers which specifically hybridize with nucleic acids encoding AvrA protein or which flank the coding region of AvrA protein, subjecting the sample to multiple steps of PCR amplification and detecting the presence or absence of the amplified sequence (e.g., using gel analysis, blotting methods, or fluorescently-labeled primers). Alternatively, an oligonucleotide, an aptamer, a cDNA, an antibody, or a fragment thereof, which interacts with at least a portion of the nucleic acids encoding AvrA protein is configured in an array on a chip or wafer and used for detecting nucleic acids encoding AvrA protein. Briefly, these techniques involve methods for analyzing large numbers of genes rapidly and accurately. By tagging genes with oligonucleotides or using fixed probe arrays, one can employ chip technology to segregate target molecules as high density arrays and screen these molecules on the basis of hybridization (see, e.g., Pease, et al. (1994) *Proc. Natl. Acad. Sci. USA* 91(11):5022-6; Fodor, et al. (1991) *Science* 251(4995):767-73).

Primers or oligonucleotides for use in this aspect of the invention can be selected from any region of the locus encoding AvrA protein and generally specifically anneal and amplify at least a portion of a nucleic acid encoding AvrA protein and no other nucleic acid encoding a closely related protein. Suitable primers for amplification of nucleic acids encoding AvrA protein include those exemplified herein (e.g., SEQ ID NO:5 and SEQ ID NO:6) or can be selected by the skilled artisan from the nucleic acid sequences encoding AvrA protein. See nucleotides 3009905 . . . 3010813 of GENBANK Accession No. AE006468 (McClelland, et al. (2001) *Nature* 413(6858):852-6).

In general, suitable primers are 12 to 30 bp in length and generate a PCR amplicon of 50, 100, 200 400, 600, 1000 bp or more in length. In accordance with this method, a geometrically amplified product is obtained only when the first and second nucleotide sequences occur within the same nucleic acid molecule encoding the AvrA protein. The fundamentals of non-degenerate PCR are well-known to the skilled artisan, see, e.g., McPherson, et al., PCR, *A Practical Approach*, IRL Press, Oxford, Eng. (1991).

As a further aspect of this invention, a serological test is used to detect an anti-AvrA antibody in a biological sample from a subject. A variety of serological assays can be used in this invention to detect antibodies to AvrA in biological samples. Well-characterized assays such as ELISAs, rapid flow-through assays, latex agglutination assays, immunoblot assays, and lateral flow immunoassays are all contemplated in this invention. By way of illustration, the serological assay is performed by an enzyme immunoassay microtiter method, wherein wells of a microtiter plate are coated with AvrA protein, a biological sample at various dilutions is added to the wells and after a suitable amount of time, the plate is washed and an enzyme-conjugated secondary antibody and appropriate substrate for the enzyme are added to the wells to determine whether the biological sample has an antibody to the AvrA protein.

As an optional feature of the instant diagnostic methods, the expression of Wnt1 is detected in colorectal epithelial cells. In accordance with this embodiment, lower levels of expression of Wnt1 in colorectal epithelial cells of the subject relative to epithelial cells that were not exposed to *Salmonella* further identifies a subject as having at least an indication or predisposition for developing colorectal cancer. A "lower level of expression" of a marker refers to an expression level in a test sample that is at least twice, and in certain embodiments, three, four, five or ten times lower than the expression level of the marker in a control sample (e.g., epithelial cells of the subject that were not previously exposed to *Salmonella* or a sample from a healthy subject not having been previously infected with *Salmonella*). Wnt1 expression can be assessed by one or more of the methods disclosed herein for assessing AvrA expression. However, in certain embodiments, Wnt1 expression is determined by measuring the level of nucleic acids encoding Wnt1 in colorectal epithelial cells using, e.g., PCR. Primers of use in accordance with this aspect include GAGC-CACGAGTTTGGATGTT (SEQ ID NO:14) and TGAG-GAGAGAAGAGGGACCA (SEQ ID NO:15)

Ideally, assays for detecting the presence of *Salmonella* AvrA protein, nucleic acids encoding *Salmonella* AvrA protein, or an anti-AvrA antibody, and optionally Wnt1 will include a positive and/or negative control to assess the accuracy of the method. Upon detecting the presence of *Salmonella* AvrA protein, nucleic acids encoding *Salmonella* AvrA protein, or an anti-AvrA antibody, the subject is identified as having at least an indication or predisposition for developing inflammatory bowel disease or colorectal cancer. As demonstrated herein an inflammatory bowel disease includes but is not limited Crohn's disease and ulcerative colitis.

In conjunction with the diagnostic method of the present invention, a kit for identifying a subject having at least an indication or predisposition for developing inflammatory bowel disease or colorectal cancer is also provided. A kit of the invention includes a container containing at least one binding agent (e.g., an antibody) that specifically binds AvrA protein; primers (e.g., those disclosed herein) for amplifying nucleic acids encoding AvrA protein and/or a substrate having adhered thereto AvrA protein. In certain embodiments, the kit includes at least one of (i) an antibody that specifically binds to amino acid residues CGEEP-FLPSDKADRY (SEQ ID NO:30) of AvrA protein; (ii) a set of primers having the nucleotide sequences of GAATG-GAAGGCGTTGAATCTGC (SEQ ID NO:5) and GTTGTGCGCCTTGAGTATGTTTGTAA (SEQ ID NO:6); or (iii) a multiwell plate, wherein wells of the plate are coated with purified AvrA protein (SEQ ID NO:31). In a further embodiment, the kit optionally includes a set of primers for amplifying nucleic acids encoding Wnt1 protein. In particular embodiments, the kit further includes a set of primers having the nucleotide sequences of GAGC-CACGAGTTTGGATGTT (SEQ ID NO:14) and TGAG-GAGAGAAGAGGGACCA (SEQ ID NO:15).

The kit can also contain other solutions necessary or convenient for carrying out the invention. The container can be made of glass, plastic or foil and can be a vial, bottle, pouch, tube, bag, etc. The kit may also contain written information, such as procedures for carrying out the present invention or analytical information, such as the amount of reagent contained in the first container means. The container can be in another container, e.g., a box or a bag, along with the written information.

The data presented herein demonstrate that *Salmonella* infection reduces Wnt1 protein expression in intestinal epithelial cells both in vitro and in vivo, wherein said reduction promotes cancer cell migration and invasion. Accordingly, the present invention is also a method for treating colorectal cancer in a subject by administering to a subject having had a previous *Salmonella* infection an effective amount of an agent that increases Wnt1 expression or activity in the subject's colorectal tissues. As used herein, an agent which increases the expression or activity of Wnt1 is intended to include Wnt protein or Wnt agonist, optionally in combination with one or more additional therapeutic compound(s).

Wnt proteins form a family of highly conserved secreted signaling molecules that regulate cell-to-cell interactions during embryogenesis. The terms "Wnts" or "Wnt gene product" or "Wnt polypeptide" when used herein encompass native sequence Wnt polypeptides, Wnt polypeptide variants, Wnt polypeptide fragments and chimeric Wnt polypeptides. A "native sequence" polypeptide is one that has the same amino acid sequence as a Wnt polypeptide derived from nature. Such native sequence polypeptides can be isolated from cells producing endogenous Wnt protein or can be produced by recombinant or synthetic means. Thus, a native sequence polypeptide can have the amino acid sequence of, e.g., naturally occurring human polypeptide, murine polypeptide, or polypeptide from any other mammalian species. A human Wnt1 protein of use in this invention includes the Wnt1 protein available under GENBANK Accession No. NP_005421.1 (SEQ ID NO:32), which is expressed in inter alia small intestine and colon.

The term "native sequence Wnt protein" includes the native protein with or without the initiating N-terminal methionine (Met), and with or without the native signal sequence. The native human and murine Wnt polypeptides known in the art are from about 348 to about 389 amino acids in length in their unprocessed form reflecting variability (particularly at the poorly conserved amino-terminus and several internal sites), contain 21 conserved cysteines, and have the features of a secreted protein. The molecular weight of a Wnt polypeptide is about 38-42 kD.

A "variant" polypeptide means a biologically active polypeptide as defined herein having less than 100% sequence identity with a native sequence polypeptide. Such variants include polypeptides wherein one or more amino acid residues are added at the N- or C-terminus of, or within, the native sequence; from about one to forty amino acid residues are deleted, and optionally substituted by one or more amino acid residues; and derivatives of the above polypeptides, wherein an amino acid residue has been covalently modified so that the resulting product has a non-naturally occurring amino acid. Ordinarily, a biologically active Wnt variant will have an amino acid sequence having at least about 90% amino acid sequence identity with a native sequence Wnt polypeptide, preferably at least about 95%, more preferably at least about 99%.

A "chimeric" Wnt polypeptide is a polypeptide including a Wnt polypeptide or portion (e.g., one or more domains) thereof fused or bonded to heterologous polypeptide. The chimeric Wnt polypeptide will generally share at least one biological property in common with a native sequence Wnt polypeptide. Examples of chimeric polypeptides include immunoadhesins, which combine a portion of the Wnt polypeptide with an immunoglobulin sequence, and epitope-tagged polypeptides, which include a Wnt polypeptide or portion thereof fused to a "tag polypeptide". The tag polypeptide has enough residues to provide an epitope against which an antibody can be made, yet is short enough such that it does not interfere with biological activity of the Wnt polypeptide. Suitable tag polypeptides generally have at least six amino acid residues and usually between about 6-60 amino acid residues.

A "functional derivative" of a native sequence Wnt polypeptide is a compound having a qualitative biological property in common with a native sequence Wnt polypeptide. "Functional derivatives" include, but are not limited to, fragments of a native sequence and derivatives of a native sequence Wnt polypeptide and its fragments, provided that they have a biological activity in common with a corresponding native sequence Wnt polypeptide. The term "derivative" encompasses both amino acid sequence variants of Wnt polypeptide and covalent modifications thereof.

Other activators of Wnt1 include compounds that bind to, and activate receptors of the Frizzled family on the cell surface, e.g., antibodies and fragments thereof, Wnt mimetics and derivatives, and the like. For example, casein kinase Iε (CKIε) has been identified as a positive regulator of the Wnt signaling pathway, for example, see Peters, et al. (1999) *Nature* 401:345-350; and Sakanaka, et al. (1999) *Proc. Natl. Acad. Sci. USA* 96:12548-12552.

The therapeutic method of the present invention will, in other embodiments, use Wnt1 protein compositions that are active when administered to an animal, e.g., a mammal, in vivo or ex vivo. One may determine the specific activity of a Wnt1 protein in a composition by determining the level of activity in a functional assay after in vivo administration, e.g., upregulation of stem cell proliferation, β-catenin stabilization, etc., quantitating the amount of Wnt1 protein present in a non-functional assay, e.g., immunostaining, ELISA, quantitation on silver stained gel, etc., and determining the ratio of in vivo biologically active Wnt1 to total Wnt1.

Wnt1 proteins can be readily prepared by conventional recombinant protein techniques, wherein recombinant host cells are transformed or transduced with an expression construct or vector harboring a nucleic acid molecule encoding the Wnt1 protein, the recombinant host cells are grown under suitable conditions to provide for expression of the Wnt1 protein, and the Wnt1 protein is subsequently isolated and optionally purified. Accordingly, this invention also provides a nucleic acid molecule encoding a Wnt1 protein, as well as an expression cassette and/or expression vector containing the same. Ideally, the expression cassette and expression vector contain the necessary regulatory sequences (e.g., promoter, terminator, and the like) to facilitate expression in the host cell of interest. Host cells including a nucleic acid molecule encoding a Wnt1 protein are also included within the scope of this invention. Host cells can include eukaryotic cells (e.g., mammalian, fungal or yeast cells) or prokaryotic cells (e.g., *E. coli*).

As an alternative embodiment of the therapeutic method of this invention, Wnt1 expression is increased using a nucleic acid molecule encoding a Wnt1 protein, or an expression cassette or expression vector containing the same. The use of gene therapy in the treatment of disease is well-known known in the art and any suitable vector and/or mode of administration can be used in the context of this invention.

When administering Wnt1 protein, lipid structures have been found to be important in maintaining activity following in vivo administration. The Wnt1 protein is not encapsulated in the aqueous phase of these structures, but are rather integrated into the lipid membrane, and may be inserted in the outer layer of a membrane. Methods for tethering Wnt1 protein to the external surface of a liposome or micelle may use a sequence so as to emphasize the exoliposomal display of the protein, where crude liposomes are first pre-formed; Wnt1 protein is then added to the crude mixture, which will favor addition of exoliposomal Wnt1, followed by various formulation steps, which may include size filtering; dialysis, and the like. Suitable lipids include fatty acids, neutral fats such as triacylglycerols, fatty acid esters and soaps, long chain (fatty) alcohols and waxes, sphingoids and other long chain bases, glycolipids, sphingolipids, carotenes, polyprenols, sterols, and the like, as well as terpenes and isoprenoids. For example, molecules such as diacetylene phospholipids may find use.

While not required for activity, in some embodiments a lipid structure may include a targeting group, e.g., a targeting moiety covalently or non-covalently bound to the hydrophilic head group. Head groups useful to bind to targeting moieties include, for example, biotin, amines, cyano-, carboxylic acids, isothiocyanates, thiols, disulfides, α-halocarbonyl compounds, α,β-unsaturated carbonyl compounds, alkyl hydrazines, etc. Chemical groups that find use in linking a targeting moiety to an amphipathic molecule include carbamate; amide (amine plus carboxylic acid); ester (alcohol plus carboxylic acid), thioether (haloalkane plus sulfhydryl, maleimide plus sulfhydryl), Schiff's base (amine plus aldehyde), urea (amine plus isocyanate), thiourea (amine plus isothiocyanate), sulfonamide (amine plus sulfonyl chloride), disulfide, hyrodrazone, lipids, and the like, as known in the art. For example, targeting molecules may be formed by converting a commercially available lipid, such as DAGPE, a PEG-PDA amine, DOTAP, etc. into an isocyanate, followed by treatment with triethylene glycol diamine spacer to produce the amine terminated thiocarbamate lipid which by treatment with the para-isothiocyanophenyl glycoside of the targeting moiety produces the desired targeting glycolipids.

A targeting moiety, as used herein, refers to a molecule capable of specifically binding to a particular target molecule and forming a bound complex. Thus, the ligand and its corresponding target molecule form a specific binding pair. Examples of targeting moieties include, but are not limited to antibodies, lymphokines, cytokines, receptor proteins such as CD4 and CD8, solubilized receptor proteins such as soluble CD4, hormones, growth factors, peptidomimetics, synthetic ligands, and the like which specifically bind desired target cells, e.g., colorectal cells. Targeting moieties of particular interest include peptidomimetics, peptides, antibodies and antibody fragments (e.g., the Fab' fragment).

For therapeutic applications, pharmaceutical compositions include a therapeutically effective dose of one or more agents that increase Wnt1 expression or activity and an optional pharmaceutically acceptable carrier. Many pharmaceutically acceptable carriers may be employed in the compositions of the present invention. Generally, normal saline will be employed as the pharmaceutically acceptable carrier. Other suitable carriers include, e.g., water, buffered water, 0.4% saline, 0.3% glycine, and the like, including glycoproteins for enhanced stability, such as albumin, lipoprotein, globulin, etc. These compositions may be sterilized by conventional, well known sterilization techniques. The resulting aqueous solutions may be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc.

The subject therapeutic method is useful for both prophylactic and therapeutic purposes. Thus, as used herein, an "effective amount" refers to an amount of an active ingredient sufficient to achieve the intended purpose of (a) reducing the severity of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); (e) limiting or preventing recurrence of symptoms in patients that were previously symptomatic for the disorder(s); (f) reduction of mortality after occurrence of a disease or a disorder; (g) healing; and (h) prophylaxis of a disease. The effective amount in each individual case may be determined empirically by a skilled artisan according to established methods in the art. As used in the context of the invention, "administering" includes in vivo administration to an individual as well as administration directly to cells or tissue in vitro or ex vivo. A clinician may titer the dosage or route of administration to obtain the optimal therapeutic effect. Evidence of therapeutic effect may be any diminution in the severity of disease. The therapeutic effect can be measured in terms of clinical outcome or can be determined by immunological or biochemical tests. Patents for treatment may be mammals, e.g., primates, including humans, may be laboratory animals, e.g., rabbits, rats, mice, etc., particularly for evaluation of therapies, horses, dogs, cats, farm animals, etc.

The dosage of the therapeutic formulation will vary widely, depending upon the nature of the condition, the frequency of administration, the manner of administration, the clearance of the agent from the host, and the like. The initial dose can be larger, followed by smaller maintenance doses. The dose can be administered as infrequently as weekly or biweekly, or more often fractionated into smaller doses and administered daily, semi-weekly, or otherwise as needed to maintain an effective dosage level.

In some embodiments of the invention, administration of the Wnt1 pharmaceutical formulation is performed by local administration. Local administration, as used herein, may refer to topical administration, but more often refers to injection or other introduction into the body at a site of treatment. In some embodiments of the invention, the formulations are administered on a short-term basis, for example a single administration, or a series of administration performed over, e.g., 1, 2, 3 or more days, up to 1 or 2 weeks, in order to obtain a rapid, significant increase in activity. The size of the dose administered must be determined by a physician and will depend on a number of factors, such as the nature and gravity of the disease, the age and state of health of the patient and the patient's tolerance to the drug itself.

Chemotherapy and therapeutic anticancer agents which will be used in conjunction with an agent that increases Wnt1 expression or activity include, cytotoxic agents such as Taxol, Cytochalasin B, Gramicidin D, Ethidium Bromide, Emetine, Mitomycin, Etoposide, Tenoposide, Vincristine, Vinblastine, camptothecin (CPT), Colchicin, Doxorubicin, Daunorubicin, Mitoxantrone, Mithramycin, Actinomycin D, 1-Dehydrotestosterone, Glucocorticoids, Procaine, Tetracaine, Lidocaine, Propranolol, blocked ricin (Lynch, et al. (1997) *J. Clin. Oncol.* 15(2):723-34) and Puromycin and analogs or homologs thereof. Therapeutic agents include, but are not limited to, antimetabolites (e.g., methotrexate, 6-mercaptopurine, 6-thioguanine, cytarabine, 5-fluorouracil, decarbazine), alkylating agents (e.g., mechlorethamine, thiotepa, chlorambucil, melphalan, carmustine, lomustine, cyclophosphamide, busulfan, dibromomannitol, streptozotocin, mitomycin C, cis-dichlorodiamine platinum (II), cisplatin), anthracyclines (e.g., daunorubicin and doxorubicin), antibiotics (e.g., dactinomycin, bleomycin, mithramycin, and anthramycin), anti-mitotic agents (e.g., vincristine and vinblastine) and selective apoptotic agents such as APTO-SYN® (exisulind), PANZEM™ (2-methoxyestradiol), and VELCADE® (bortezomib). Radiotherapeutic agents which can be targeted to neuroendocrine tumors via binding agents are well-known in the art. See, e.g., Ballangrud, et al. (2004) *Clin. Cancer Res.* 10(13):4489-97.

The invention is described in greater detail by the following non-limiting examples.

EXAMPLE 1

Materials and Methods

Human Samples. Human fecal DNA samples used for this study were a part of deidentified samples from a previous study where stool specimens were collected from noncancer volunteers in Metropolitan Detroit. Details concerning the parent study have been reported elsewhere (Yu, et al. (2008) *Cancer Epidemiol. Biomarkers Prev.* 17(2):455-8; Nechvatal, et al. (2008) *Microbiol. Methods* 72(2):124-32; Kato, et al. (2009) *Tumori* 95(6):753-61; Kato, et al. (2010) *Med. Sci. Monit.* 16(1):CR1-7). The human tissue microarrays (TMAs) used in this study were purchased from US Biomax.

Moderate and highly differentiated human adenocarcinoma samples were obtained from Guangdong Institute of Gastroenterology, the Sixth Affiliated Hospital, Sun Yat-Sen University, China in accordance with approval from the institute.

Animals. C57BL/6 mice (Female, 6-8 weeks old) were obtained from the Jackson Laboratory (Jackson Laboratory, Bar Harbor, Me.). All animal work was approved by University of Rochester and University of Illinois at Chicago Committee on Animal Resources. Euthanasia was accomplished via sodium pentobarbital (100 mg per kg body weight) i.p., followed by cervical dislocation. All methods were carried out in accordance with the approved guidelines by Committees on Animal Resources.

Bacterial Strains and Growth Conditions. *Salmonella* strains used in this study included *Salmonella* mutant strains Phop$^c$AvrA$^-$/AvrA$^+$, wild-type *Salmonella enterica* serovar Enteritidis (S.E) C50336 or wild-type *Salmonella* Typhimurium SL1344 (SB300), AvrA mutant S.E-AvrA$^-$ and the complemented strain S.E-AvrA$^+$ (Table 1). Bacterial cultures were prepared by inoculating 5-10 ml of Luria-Bertani broth with 0.01 ml of a stationary-phase culture followed by overnight incubation (>18 hours) at 37° C.

TABLE 1

| Strain | Characteristics | Reference |
|---|---|---|
| S.E-WT | *Salmonella enteritidis* wild type CMCC(B)50336 | Lin, et al. (2016) *J. Biol. Chem.* 291(52): 26837-49 |
| SB300 | *Salmonella Typhimurium* wild type SL1344 | |
| S.E-AvrA$^-$ | C50336 AvrA-deficient mutant | |
| S.E-AvrA$^+$ | C50336 AvrA-deficient mutant carrying pBR322-AvrA | |
| PhoP$^c$ | Non-pathogenic complex regulator mutant derived from wild-type SL 14028 | Lu, et al. (2014) *Oncogenesis* 3: e105; Lu, et al. (2012) *Am. J. Physiol. Gastrointest. Liver Physiol.* 303(10): G1113-25 |
| PhoP$^c$AvrA$^-$ | AvrA$^-$ mutation derived from PhoP$^c$ | |
| PhoP$^c$AvrA$^-$/AvrA$^+$ | PhoP$^c$AvrA$^-$ with complemented plasmid encoding AvrA | |

Real-Time PCR of Bacterial 16sRNA and *Salmonella*. Real-time PCR was used to amplify universal bacterial 16sRNA, *Salmonella* 16S-23S internal transcribed spacer (ITS), as well as *Salmonella* AvrA. Total DNA was extracted from human fecal material using a kit sold under the trademark Qiagen® Stool Kit by Qiagen. DNA was subjected to real-time PCR using the primers listed in Table 2 and a kit sold under the trademark SYBR® Green PCR kit by BIORAD. Percent expression was calculated as the ratio of the normalized value of each sample relative to that of the corresponding control group. All real-time PCR reactions were performed in triplicate.

TABLE 2

| Primer | Sequence | SEQ ID NO: |
|---|---|---|
| Univ bacteria 16s F | TCCTACGGGAGGCAGCAGT | 1 |

TABLE 2-continued

| Primer | Sequence | SEQ ID NO: |
|---|---|---|
| Univ bacteria 16s R | GGACTACCAGGGTATCTAATCCTGTT | 2 |
| *Salmonella* ITS F | TATGCCCCATCGTGTAGTCAGAAC | 3 |
| *Salmonella* ITS R | TGCGGCTGGATCACCTCCTT | 4 |
| *Salmonella* AvrA F | GAATGGAAGGCGTTGAATCTGC | 5 |
| *Salmonella* AvrA R | GTTGTGCGCCTTGAGTATGTTTGTAA | 6 |

*Salmonella*-Infected Mouse Model. Animal experiments were performed using specific pathogen-free female C57BL/6 mice. Water and food were withdrawn 4 hours before oral gavage with 7.5 mg/mouse of streptomycin (100 ml of sterile solution). Afterward, animals were supplied with water and food ad libitum. Twenty hours after streptomycin treatment, water and food were withdrawn again for 4 hours before the mice were infected with $1\times10^6$ or $1.0\times10^8$ colony-forming units (CFU) of *Salmonella* (100-µl suspension in HBSS (Hank's Balanced Salt Solution) or treated with sterile HBSS (control) by oral gavage as previously described (Lu, et al. (2012) *Am. J. Physiol. Gastrointest. Liver Physiol.* 303(10):G1113-25; Lu, et al. (2010) *PLoS ONE* 5(5):e10505). After *Salmonella* gavage, tissue samples were collected at 8 hours and 4 days for the short-term model and at 1, 3, 10, 27 weeks for *Salmonella*-chronically infected model.

*Salmonella*-Infected Colon Cancer Mouse Model. Animal experiments were performed by using specific pathogen-free female C57BL/6 mice (Taconic) that were 6-7 weeks old, as previously described (Duan, et al. (2007) *Lab. Invest.* 87(6): 613-24). Water and food were withdrawn 4 hours before oral gavage with 7.5 mg/mouse of streptomycin (100 µl of sterile solution). Afterward, animals were supplied with water and food ad libitum. Twenty hours after streptomycin treatment, water and food were withdrawn again for 4 hours before the mice were infected with $1\times10^6$ CFU of *S. typhimurium* (100-µl suspension in HBSS) or treated with sterile HBSS (control) by oral gavage, as previously described (McCormick, et al. (1993) *J. Cell Biol.* 123(4):895-907). After *Salmonella* gavage, AOM/DSS were administrated as follows: azoxymethane (AOM), 10 mg/kg body weight, intraperitoneal injection, 1% dextran sodium sulfate (DSS) in drinking water. At indicated time points after *Salmonella* infection (e.g., 1, 3, 6, 10 and 45 or 49 weeks), tissue samples were collected. Tumors and paired adjacent "normal" mucosa from colon were collected from mice 49 weeks post-infection.

Immunohistochemistry (IHC). Intestinal tissues were freshly collected and embedded in paraffin wax after fixation with a 10% neutral buffered formalin. Immunohistochemistry was performed on paraffin-embedded sections (4 µl) of colons (mouse or human). After preparation of the slides by conventional methods (Ye, et al. (2007) *Am. J. Pathol.* 171(3)882-92; Lu, et al. (2014) *Oncogenesis* 3:e105; Lu, et al. (2012) *Am. J. Physiol. Gastrointest. Liver Physiol.* 303 (10):G1113-25; Liu, et al. (2010 *FEBS Lett.* 584(5):911-16) slides were incubated in 3% hydrogen peroxide for 20 minutes at room temperature to block endogenous peroxidase activity, followed by incubation for 30-60 minutes in 2% bovine serum albumin (BSA) in phosphate-buffered saline (PBS) to reduce nonspecific background.

For AvrA analysis, the slides were incubated with anti-AvrA antibody at 4° C. overnight. Samples were then incubated with goat anti-rabbit antibody (Jackson Immu-noResearch, West Grove, Pa.) for 1 hour at room temperature. Anti-AvrA antibody was custom-made. See Wu, et al. (2010) *Am. J. Physiol. Gastrointest. Liver Physiol.* 298(5): G784-94.

For Wnt1 and β-catenin analysis, the slides were incubated with anti-Wnt1 (1:100, Cell Signaling) and anti-β-catenin (1:100; BD, San Jose, Calif.) for 10-12 hours at 4° C. Samples were then incubated with DAPI for 10 minutes at room temperature. Tissues were mounted with antifade reagent sold under the trademark SLOWFADE® (Molecular Probes) and then a cover slip was applied. The edges were sealed to prevent drying. Specimens were examined with a Leica SP5 scanning confocal microscope.

*Salmonella* Anti-AvrA Antibody Enzyme-Linked Immu-nosorbent Assay (ELISA). *Salmonella* AvrA antibody in mouse serum was measured using an AvrA antibody ELISA. The 96-well plate was coated with purified AvrA protein (1 μg/ml) at 4° C. overnight. The coated plate was subsequently blocked with 1% BSA at 4° C. overnight. Mouse serum (100 μl per well, 1:5 dilution) was added to the well for 2 hours in a 37° C. incubator. Following complete washing, 1:300 diluted horseradish peroxidase (HRP)-conjugated goat anti-mouse antibody (BioRad) was added to each well for 1 hour at 37° C. Following complete washing, KPL SureBlue™ peroxidase substrate was added. The absorbance of each well was subsequently measured at 450 nm. Anti-AvrA antibody (1:100 and 1:1000) was used as a positive control and 1% BSA as a negative control.

Statistical Analysis. Generally, descriptive statistics for continuous variables were expressed as mean±standard deviation (SD), categorical variables were presented as frequency and proportion. For AvrA staining scores, mean, median, and quartile were reported. All statistical tests were two sided. P values of 0.05 or less were considered statistically significant.

Data were expressed as mean±SD. Differences between two samples were analyzed by Student's t-test with Graph-Pad Prism 5 and differences among three or more groups were analyzed using one-way ANOVA. IHC of AvrA staining was initially assessed as a product of staining intensity (0, 1, 2, 3, 4=no staining, minimal, slight, moderate, marked intensity, respectively) and percentage of cells stained (1, 2, 3, 4, 5=few scattered (occasional cells), several scattered cells, focal (one or a few areas or cells), multifocal (several areas of cells), diffuse (most cells), respectively) ranging from 0 to 20. Out of the 168 cores scored on three tissue microarray (TMA) slides, hyperplasia (n=8) was excluded due to too small sample size as a single diagnostic category. Further, only one of the cores with the highest staining score was taken for the 5 paired samples derived from same patients present within the same TMA slides. As a result, the final analytical sample was composed of 155 unique cores. The comparison of the results of the three TMA slides revealed substantial staining variability among slides, specifically generally much stronger staining in the first slide, much weaker in the second and even weaker in the third. Thus, to combine results from three TMA slides, normalized staining scores were calculated based on relative rankings of individual core staining within each slide to generate normalized scores centered at 0. To make all scores positive, each score was added to the lowest score among all TMAs.

As a result, the final normalized scores ranged from 0 to 4. These results were summarized in Table 3.

TABLE 3

| TMA Name | N | AvrA Scores | Mean | Median | Quartile 1 | Quartile 3 |
|---|---|---|---|---|---|---|
| CO808-036 | 58 | Raw | 10.103 | 10.00 | 6.00 | 15.00 |
|  |  | Normalized | 1.771 | 1.77 | 1.07 | 2.57 |
| CO809a-C051 | 57 | Raw | 2.158 | 1.00 | 0.00 | 2.00 |
|  |  | Normalized | 1.771 | 1.66 | 0.66 | 2.36 |
| BC05002a-E068 | 40 | Raw | 1.175 | 1.00 | 0.00 | 1.00 |
|  |  | Normalized | 1.771 | 2.10 | 0.87 | 2.10 |

Analysis of variance was used to test differences in mean normalized scores across 5 different colorectal pathologies (inflammation, adenoma, cancer adjacent mucosa, colorectal cancer and metastasized lymph nodes) from normal mucosa. The statistical analyses were conducted by SAS version 9.4 (SAS Institute Inc., Cary, N.C., USA).

Human Cell Culture. Human colonic epithelial HCT116, Caco-2 and SKCO-15 cells were maintained in Dulbecco's modified Eagle's medium (DMEM) supplemented with 10% fetal bovine serum (FBS), penicillin-streptomycin and L-glutamine at 37° C., as previously described (Liu, et al. (2011) *Am. J. Physiol. Gastrointest. Liver Physiol.* 301(6): G992-G1003).

*S. typhimurium* Attachment and Invasion of Human Epithelial Monolayers. HCT116 cells were infected with *S. typhimurium* according to established methods (McCormick, et al. (1993) *J. Cell Biol.* 123(4):895-907). For bacterial attachment, cells were stimulated with *Salmonella* for 0.5 hour, and washed with PBS for the cell-associated bacteria. Subsequently, 0.9 ml LB broth was added, and each sample was mixed vigorously and quantified by plating for colony-forming units (CFUs) on MacConkey agar medium. Bacterial invasion was assessed after bacterial solutions (~20 bacteria/epithelial cell) had been added for 30 minutes. Bacteria internalized in epithelial cells were released with 1% Triton™ X-100 after gentamicin (50 μg/ml) treatment for 20 minutes. Gentamicin does not permeate eukaryotic plasma membranes and therefore is cytolytic to only extracellular populations of bacteria; intracellular bacteria populations remain viable (Lissner, et al. (1983) *J. Immunol.* 131(6):3006-13). To quantitate internalized bacteria, 0.9 ml of LB was then added, the sample was vigorously mixed, and CFUs were quantitated by plating on MacConkey agar medium (Liu, et al. (2012) *Inflamm. Bowel Dis.* 18(3):418-29).

Design of the Wnt1 Single Guide RNA Sequences. Single guide RNA (sgRNA) sequences targeting the coding sequence of Wnt1 were selected using the online CRISPR design tool from the Zhang lab at the Broad Institute. The following sgRNAs, which were cloned into the Crispr-Cas9-V2-Puro vector (Cong, et al. (2013) *Science* 339(6121):819-23), were predicted to have a very low probability of off-target sites: sgRNA1 5'-TGC-TACGCTGCTGCTGGCGC-3' (SEQ ID NO:7), sgRNA2 5'-GGCAGTTCCGGAATCTCCTC-3' (SEQ ID NO:8), and sgRNA3 5'-GACAGTTCCAGCGGCGATTC-3' (SEQ ID NO:9).

Characterizing Wnt1-Knockout (KO) Lines. Western blot analysis confirmed that the Wnt1 KO cells expressed lower levels of Wnt1 protein. Specifically, cell lysates from wild-type and KO HCT116 cells were separated by SDS-PAGE, transferred to PVDF membranes, and then blotted with an anti-Wnt1 antibody (Bioworld) with an anti-actin antibody (Bioworld) used as the loading control.

Construction of the Plasmid pcDNA3.1-hWnt1. The pCDNA3.1-hWnt1 (6.615 kb) plasmid was constructed by inserting an EcoRI-XbaI fragment containing the human Wnt1 complementary DNA (cDNA) (1.113 kb) into the pCDNA3.1-His plasmid (5.502 kb). PCR primers for generating the EcoRI-XbaI fragment containing the hWnt1 cDNA were as follows:

```
EcoRI-hWnt1 forward primer:
                                     (SEQ ID NO: 10)
5'-CGGAATTCATGGGGCTCTGGGCGCTGTT-3';

hWnt1-XbaI reverse primer:
                                     (SEQ ID NO: 11)
5'-GCTCTAGACAGACACTCGTGCAGTACGC-3'.
```

Immunoprecipitation. The cells were rinsed twice in ice-cold HBSS and were lysed in ice-cold immunoprecipitation buffer (1% Triton™ X-100, 150 mmol/L NaCl, 10 mmol/L Tris, pH 7.4, 1 mmol/L EDTA, 1 mmol/L ethylene glycol bis (β-aminoethyl ether)-N,N,N',N'-tetraacetic acid, pH 8.0, 0.2 mmol/L sodium orthovanadate, and protease inhibitor cocktail (Roche Diagnostics, Basel, Switzerland)). The samples were prepared as previously described (Sun, et al. *Am. J. Physiol. Gastrointest. Liver Physiol.* 289:G129-137). The blots were probed with anti-HA-probe (1:1000, Santa Cruz Biotechnology, Inc., Santa Cruz, Calif.) and anti-c-myc (Santa Cruz Biotechnology, Inc., Santa Cruz, Calif.) antibodies.

Co-Immunoprecipitation Assay. Cells were rinsed twice in ice-cold PBS and lysed in cold lysis buffer (1% Triton™ X-100, 150 mM NaCl, 10 mM Tris-HCl, pH 7.4, 1 mM EDTA, 1 mM EGTA, pH 8.0, and 0.2 mM sodium orthovanadate) containing a protease inhibitor cocktail. Samples were pre-cleared with protein A-agarose. Pre-cleared lysates were incubated with 2 μg of anti-ubiquitin (Enzo life Science, Plymouth Meeting, Pa.) or anti-IgG (Cell Signaling) primary antibodies overnight at 4° C. Protein A-agarose was added to the lysate, and the mixture was incubated for 2-3 hours with agitation at 4° C. The precipitate was pelleted by centrifugation at 3000 rpm for 5 minutes, the supernatant was removed, and the pellet was washed four times (twice with lysis buffer, once with TBS and once with 0.05 M Tris-HCl). The pellet was resuspended, boiled for 5 minutes, separated by SDS-polyacrylamide gel electrophoresis, and transferred onto a nitrocellulose membrane. Membranes were probed with an infrared-conjugated secondary antibody, and the signals were visualized and quantitated using LI-COR Odyssey v3.0 software.

Real-Time Quantitative PCR Analysis. Total RNA was extracted from epithelial cell monolayers using TRIzol™ reagent (Life Technology). RNA integrity was verified by gel electrophoresis. RNA was reverse-transcribed using the 5× All-In-One RT MasterMix (Applied Biological Materials Inc.) according to the manufacturer's directions. The RT cDNA reaction products were subjected to quantitative real-time PCR using a qPCR kit sold under the tradename EVAGREEN® 2× qPCR MasterMix-No Dye (Applied Biological Materials Inc.) according to the manufacturer's instructions. The following primers for β-actin, WNT1, IL-8, IL-6 and GM-CSF were used: β-actin forward 5'-AGAGCAAGAGAGGGCATCCTC-3' (SEQ ID NO:12), β-actin reverse 5'-GACGGCCGCATCTTCTTGT-3' (SEQ ID NO:13), WNT1 forward 5'-GAGCCACGAGTTTGGATGTT-3' (SEQ ID NO:14), WNT1 reverse 5'-TGAGGAGAGAAGAGGGACCA-3' (SEQ ID NO:15), IL-8 forward 5'-TGCATAAAGACATACTCCAAACCT-3' (SEQ ID NO:16), IL-8 reverse 5'-AATTCTCAGCCCTCTTCAAAAA-3' (SEQ ID NO:17), IL-6 forward 5'-AGTGGCTGCAGGACATGACAA-3' (SEQ ID NO:18), IL-6 reverse 5'-CAATCTGAGGTGCCCATGCTA-3' (SEQ ID NO:19), GM-CSF forward 5'-GGCGTCTCCTGAACCTGAGT-3' (SEQ ID NO:20), GMCSF reverse 5'-GGGGATGACAAGCAGAAAGT-3' (SEQ ID NO:21), TIMP3 forward 5'-TCCCAGCGCAAGGGGCTGAA-3' (SEQ ID NO:22), TIMP3 reverse 5'-GCCGGATGCAGGCGTAGTGTT-3' (SEQ ID NO:23), Nm23 forward 5'-ACCTGAAGGACCGTCCATTCTTTGC-3' (SEQ ID NO:24), Nm23 reverse 5'-GTGAAACCACAAGCCGATCTCCT-3' (SEQ ID NO:25), c-myc forward 5'-TCAAGAGGCGAACACACAAC-3' (SEQ ID NO:26), c-myc reverse 5'-GGCCTTTTCATTGTTTTCCA-3' (SEQ ID NO:27); FlnA forward 5'-GCCAGAAGAGCAGCTTCACA-3' (SEQ ID NO:28), and FlnA reverse 5'-CCTTGAGCAGGTAGGACACG-3' (SEQ ID NO:29).

Western Blot Analysis of Mouse Intestinal Epithelial Cells in vivo. Mouse intestinal epithelial cells were lysed in lysis buffer (1% Triton™ X-100, 150 mM NaCl, 10 mM Tris, pH 7.4, 1 mM EDTA, 1 mM EGTA, pH 8.0, 0.2 mM sodium orthovanadate, and protease inhibitor cocktail), and the protein concentration was measured using Protein Assay Kits (Bio-Rad, Hercules, Calif.). The cells were rinsed two times in ice-cold HESS, lysed in protein loading buffer (50 mM Tris, pH 6.8, 100 mM dithiothreitol, 2% SDS, 0.1% bromophenol blue, and 10% glycerol), and sonicated. Equal amounts of protein were separated by SDS-PAGE, transferred to nitrocellulose membranes, and subjected to immunoblotting with primary antibodies.

Organoid cells were rinsed three times in ice-cold HBSS and were then suspended in ice-cold HESS. The organoid cells were then spun down at 900 rpm for 10 minutes at 4° C. Next, using a pipette to aspirate the PBS at the top, the organoid cells were lysed in lysis buffer and were then sonicated. The protein concentration was then measured. Equal amounts of protein were separated by SDS-polyacrylamide gel electrophoresis and were transferred to nitrocellulose membranes.

Nonspecific sites were blocked with 5% bovine serum albumin (BSA) in TEST (50 mM Tris, 150 mM NaCl, and 0.05% nonionic detergent sold under the trademark Tween® 20 adjusted to pH 7.6 with HCl), and the membranes were then incubated with dilutions of the primary antibodies as recommended by the manufacturers. The primary antibodies included the following: anti-p62 (1:1000, ABGENT, San Diego, Calif.); anti-LC3B (1:1000), anti-SAPK/JNK (1:1000), anti-phospho-SAPK/JNK (Thr183/Tyr185, 1:1000), anti-c-jun (1:1000), anti-Wnt1, anti-phospho-c-jun (1:1000) (Cell Signaling, Beverly, Mass.); anti-BECN1/Beclin-1 (1:1000), anti-c-myc (1:1000), anti-villin, anti-HA-probe (1:1000) (Santa Cruz Biotechnology, Inc., Santa Cruz, Calif.); anti-β-actin (1:2000, Sigma-Aldrich); anti-ubiquitin (1:1000, ENZO, Farmingdale, N.Y.); and anti-AvrA (1:1000).

The membranes were washed and incubated with an HRP-conjugated secondary antibody (anti-mouse, 1:5000; anti-rabbit, 1:5000; anti-goat, 1:5000; Invitrogen, Grand Island, N.Y.). The membranes were then washed again, treated with the ECL Western Blotting Substrate (Thermo Scientific, Rockford, Ill.) and visualized on X-ray film. The membranes that were sequentially probed with more than one antibody were stripped in stripping buffer (Thermo Scientific, Rockford, Ill.) before re-probing. Bands were quantified using Kodak MI software (version 4.0.3).

Transient Transfection. Transient transfections were performed with DNA transfection reagent sold under the trademark LIPOFECTAMINE® 2000 (Invitrogen) in accordance with the manufacturer's instructions. At the indicated times after transfection, protein was extracted with RIPA buffer (50 mM Tris-HCl, pH 8.0, 150 mM sodium chloride, 1.0% NP-40, 0.5% sodium deoxycholate, and 0.1% SDS) and analyzed by immunoblotting.

Western Blot Analysis of Cell Line Proteins. Infected or control cells were rinsed twice in ice-cold HESS and lysed in protein loading buffer (50 mM Tris, pH 6.8, 100 mM dithiothreitol, 2% SDS, 0.1% bromophenol blue, and 10% glycerol). Equal amounts of protein were separated by SDS-polyacrylamide gel electrophoresis, transferred to nitrocellulose membranes, and analyzed by immunoblotting with anti-Wnt1 and anti-β-actin antibodies (Bioworld). The signals were visualized and quantitated using LI-COR Odyssey v3.0 software after probing the membranes with an infrared-conjugated secondary antibody.

Cytokine Production Assay in Culture Supernatant. HCT116 cells were cultured in DMEM, followed by $Salmonella$-containing HESS ($1.6 \times 10^{10}$ bacteria/ml) for 30 minutes, washed 3 times in HESS and incubated at 37° C. for 6 hours. Cell supernatants were removed and assayed for IL-8, IL-6, and GM-CSF using an ELISA kit (Nanjing Jiancheng Company, China) in 96-well plates as described previously (Liu, et al. (2012) Inflamm. Bowel Dis. 18(3):418-29).

Cell Migration and Invasion Assay. In vitro cell migration and invasion assays were performed as previously described (Li & Zhou (2016) Neuroscience 324:131-9). Cells growing in the log phase were trypsinized, re-suspended in serum-free medium, and seeded into chambers (8-μm pore size polycarbonate membrane; Corning). The chambers were coated with a solubilized basement membrane preparation sold under the trademark MATRIGEL® (BD Biosciences) for cell invasion assays. Medium with 20% FBS (750 μl) was added to the lower chamber. After incubation for 72 hours, the cells on the top surface of the insert were removed with a cotton swab. Cells that had migrated to the bottom surface of the insert were stained with 0.1% crystal violet for 30 minutes, rinsed in PBS and subjected to microscopic inspection. Images of four random fields (10×) were captured from each membrane, and the number of migratory or invasive cells was counted. The migration and invasion results were normalized to cell number under the same treatment conditions. Triplicate assays were performed for each experiment.

Mouse Intestinal Organoid Isolation, Culture and Passage. Mouse small intestines were removed immediately after cervical dislocation. The stool was then flushed out with ice-cold PBS (penicillin, 100 I.U./mL/streptomycin, 100 μg/mL), and the small intestines were dissected, opened longitudinally and cut into ~1 cm pieces. The tissues were incubated in PBS with 2 mmol/L ethylenediamine tetraacetic acid (EDTA) for 30 minutes at 4° C. with agitation and were subsequently switched to PBS with 54.9 mmol/L D-sorbitol and 43.4 mmol/L sucrose. The tissues were then vortexed for 1-2 minutes and filtered through a 70 μm sterile cell filter. The crypts were collected by centrifugation at 150 g for 10 minutes at 4° C. Approximately 500 crypts were suspended in 50 μL of growth factor-reduced phenol-free solubilized basement membrane sold under the trademark MATRIGEL® (BD Biosciences, San Jose, Calif.). Next, a 50 μL droplet of the crypt mixture was placed in the center well of a 12-well plate. After 30 minutes of polymerization, 650 μL of the mini gut medium was overlain (Zhang, et al. (2014) Physiological reports 2:e12147; Wang, et al. (2014) PloS ONE 9:e93608). The mini gut medium (advanced DMEM/F12 supplemented with HEPES, L-glutamine, N2 and B27) was added to the culture, along with R-Spondin, Noggin, and EGF. The medium was changed every 2-3 days. For passage, the organoids were removed from the basement membrane, broken up mechanically by passage through a syringe and needle (27G, BD Biosciences, San Jose, Calif.), and transferred to fresh solubilized basement membrane. The passage was performed every 7-10 days with a 1:4 split ratio.

Bacterial Colonization. Polarized human epithelial cells were grown in DMEM with 10% FBS. At 90-100% confluence, the cells were colonized with an equal number of the indicated $Salmonella$ Enteritidis strain for 30 minutes, washed with Hank's balanced salt solution (HBSS), and incubated in DMEM containing gentamicin (100 μg/ml) for 30 minutes. The first 30 minutes of the incubation allowed the bacteria to contact the epithelial cell surface and inject the effectors into the host cells (Wu, et al. (2010) Am. J. Pathol. 177:686-697; Wu, et al. (2010) J. Visual. Exper. 39:947). After extensive HBSS washing, the extracellular bacteria were washed away. The incubation with gentamicin inhibited the bacterial growth (Sun, et al. (2004) Am. J. Physiol. Gastrointest. Liver Physiol. 287:G220-227). At the indicated times, post-colonization, the cells samples were harvested for the analysis.

The organoids (6 days after passage) were colonized with the indicated $Salmonella$ Enteritidis strain for 30 minutes, washed with HBSS, and incubated in mini gut media containing gentamicin (500 mg/mL) for the indicated times, as previously described (Zhang, et al. (2014) Physiological reports 2:e12147). After extensive HBSS washing, the extracellular bacteria were washed away. The incubation with gentamicin inhibited the growth of the bacteria. Samples were collected for a western blot analysis after the organoids were colonized with $Salmonella$ for 30 minutes and were then incubated in medium with gentamicin for 1 hour.

Cell Treatment with the JNK Inhibitor SP600125. The JNK inhibitor SP600125 (50 mM, EMD Biosciences, San Diego, Calif.) was added directly to the culture medium one hour before $Salmonella$ treatment. The HCT116 cells were pretreated with SP600125 and were incubated with the indicated $Salmonella$ for 30 minutes, washed 3 times in HBSS, incubated in DMEM containing 100 μg/ml gentamicin and 50 μM SP600125 for 30 minutes, and harvested. The protein levels were determined by western blot analysis.

Cell Treatment with the Proteasome Inhibitor MG262. To generate the ubiquitinated Beclin-1 (ub-Beclin-1) substrates for the reaction, the HCT116 cells were treated with the 40 μmol/L of MG262 proteasome inhibitor (Boston Biochem, Cambridge, Mass., USA) for 2 hours before harvesting the cells samples for analysis.

Fluorescent Staining. Fluorescent staining was performed using the fluorescent reagent sold under the trademark LYSOTRACKER® following the manufacturer's protocol (Life technologies). The HCT116 cells were grown in the Lab-Tek Chambered Coverglass System (Thermo Scientific, Rockford, Ill.), and the cells were then incubated with 100 nM LYSOTRACKER® Deep Red Probe (Life technologies, Eugene, Oreg.) in cell growth medium at 37° C. for minutes. After washing with HBBS, the cells were incubated with the indicated $Salmonella$ for 30 minutes, washed 3 times in HBSS, incubated in DMEM containing 100 μg/ml gentamicin for 30 minutes, and the cells were detected by fluorescence microscopy (ECLIPSE E600, Nikon Instruments, Inc., Melville, N.Y.).

Streptomycin Pre-Treated *Salmonella* Mouse Model. Water and food were withdrawn 4 hours before an oral gavage with 7.5 mg/mouse streptomycin. Afterward, the animals were supplied with water and food. Twenty hours after the streptomycin treatment, water and food were once again withdrawn for 4 hours before the mice were infected with $1.0 \times 10^8$ colony forming units (CFU) of *Salmonella* (100 µl bacterial suspension in HBSS) or treated with sterile HESS (control) by oral gavage, as previously described28. At the indicated times post-infection, the mice were sacrificed, and the intestinal tissue samples were removed for the analysis.

Immunofluorescence. The ileal tissues from the distal portion of the ileum were freshly isolated and paraffin-embedded after fixation with 10% neutral-buffered formalin. Immunofluorescence was performed on the paraffin-embedded sections (5 µm). After preparation of the slides (Lu, et al. (2010) *PloS ONE* 5:e10505), the tissue samples were incubated with the indicated primary antibody, anti-lysozyme (1:100, Santa Cruz Biotechnology, Inc., Santa Cruz, Calif.), at 4° C. overnight. The samples were then incubated with the sheep anti-goat antibody conjugated to the fluorescent dye sold under the trademark ALEXA FLUOR® 594 (Life Technologies, Grand Island, N.Y.) and DAPI (Life Technologies, Grand Island, N.Y.) for 1 hour at room temperature. The tissues were mounted with antifade reagent sold under the trademark SLOWFADE® (Life technologies, Grand Island, N.Y.), followed by a coverslip, and the edges were sealed to prevent drying. The specimens were examined with a Zeiss laser scanning microscope 710 (Carl Zeiss, Inc., Oberkochen, Germany).

Paneth Cell Staining and Counting. The Paneth cells in the mouse ileal tissue were counted after the anti-lysozyme immunofluorescence staining, according to established methods (Wu, et al. (2015) *Gut* 64:1082-1094). Patterns of lysozyme expression in the Paneth cells were classified into four categories as follows: normal (D0); disordered (D1); depleted (D2) and diffuse (D3), according to previously published methods (Cadwell, et al. (2008) *Nature* 456:259-263).

Paneth Cell Colonization. An improved method based on crypts isolation and digestion was set up to purify $CD24^+$ Paneth cells from mouse small intestine efficiently (Sato, et al. (2011) *Nature* 469:415-418). The purified paneth cells were distributed into 1.5 ml tubes with 200,000 cells for each in volume of 100 µl. The purified paneth cells were colonized with the indicated *Salmonella* Enteritidis strain for 1 hour, washed with HESS, and incubated in medium with gentamicin for 1 hour.

AP-1 Transcriptional Activity Assay. The cells were transiently transfected with 1 µg of pGL3-AP1 plasmid using the DNA transfection reagent sold under the trademark LIPOFECTAMINE® 3000 transfection kit, according to the manufacturer's instructions (Invitrogen, Carlsbad, Calif.). The pRL-TK vector was used as an internal control reporter. After 24 hours post-transfection, the cells were colonized with equal numbers of bacteria for 30 minutes, washed, and incubated in DMEM containing gentamicin (100 µg/ml) for 30 minutes. The luciferase activity was monitored using the dual luciferase assay system (Promega).

EXAMPLE 2

*Salmonella* Infection and Colorectal Cancer

It has now been found that AvrA, a bacterial protein from *Salmonella* enterica, is present in inflamed, colorectal tumor and precursor lesions of both animal experimental infection models and human clinical specimens. Using an AvrA serological assay, the presence of anti-*Salmonella* AvrA antibody was detected in chronic infected mouse serum samples. Further, the expression of AvrA gene in healthy human fecal samples was analyzed to advance etiological studies of *Salmonella* AvrA in the human population. This analysis indicates a potential role of this bacterial protein in human colorectal cancer. Moreover, the serological assay serves as a useful tool to identify individuals at increased risk for colorectal cancer.

Detectable Anti-AvrA Antibody in Mouse Serum Samples. An ELISA assay was developed to test the existence of anti-AvrA antibody in mice post-*Salmonella* infection. Combinations of different dilutions of antigen and antibodies were tested for titration. Subsequently, the assay was applied to mouse serum from a long-term experimental *Salmonella* infection model and *Salmonella*-infected mice of an AOM/DSS colon cancer model (Lu, et al. (2014) *Oncogenesis* 3:e105) (FIG. 1). In these experiments, anti-AvrA antibody was used as the positive control and 1% BSA as a negative control. This analysis demonstrated a significant increase in the amount of anti-AvrA antibody present in mouse serum at 10 and 27 weeks post-AvrA-positive *Salmonella* infection (FIG. 1). Likewise, *Salmonella*-infected mice in the AOM/DSS colon cancer model exhibited a significantly elevated level of anti-AvrA antibody in serum 45 weeks post Salmonella-infection (FIG. 1).

Location of AvrA in *Salmonella*-Infected Mouse Colon. Immunohistochemistry (IHC) was used to examine the location of AvrA in *Salmonella enterica* serovar Enteritidis (*S. Enteritidis*)-infected mouse colon post-infection. Mice were infected with either *S. Enteritidis* $AvrA^+$ or *S. Enteritidis* $AvrA^{-/-}$. While no positive AvrA staining was found in the *S. Enteritidis* $AvrA^{-/-}$ group at 8 hours and 4 days post-infection, IHC analysis demonstrated strong nuclear staining of many epithelial cells and some sub-epithelial stroma in the *S. Enteritidis* $AvrA^+$ group at these time points. Likewise, in the chronically-infected mouse colon, positive AvrA staining was evident at 1, 3, 10, and 27 weeks post-infection. These data indicate the persistent expression of AvrA in the *Salmonella*-infected colon.

In the chemical carcinogenesis AOM/DSS model, colorectal tumor incidence markedly increases in $AvrA^+$ *Salmonella*-infected mice, compared to mice without bacterial gavage or infected with $AvrA^-$ *Salmonella* (Lu, et al. (2014) *Oncogenesis* 3:e105). Accordingly, similar analysis was carried out to assess the presence of AvrA in the colon of *Salmonella*-infected mice of the AOM/DSS colon cancer model. In this model, strong nuclear staining of AvrA was observed in colons with tumor from AOM+DSS+ $PhoP^cAvrA^-/AvrA^+$ mice at 48 weeks post-infection. In contrast, no AvrA expression was observed in tumors from AOM+DSS+ mice infected with $PhoP^cAvrA^-$ *Salmonella* or AOM+DSS+ mice without *Salmonella* infection. Taken together, these analyses indicate persistent AvrA staining in the colon infected with an AvrA-expressing *Salmonella* strain.

AvrA Expression in Human Inflammatory Bowel Disease and Colon Samples. To demonstrate the use of this assay in humans, the presence of AvrA protein in inflammatory bowel disease (IBD) and colorectal tumor tissue of human clinical samples was examined. IHC data from cancer, Crohn's disease, and ulcerative colitis tissue samples clearly showed dense red staining of AvrA in both the cytosol and nuclei, whereas AvrA staining was negative in normal colon under both low and high power analysis.

AvrA Staining in Human TMA Samples. Three TMAs were selected for this study based upon variable numbers of colorectal histologies in different proportions (Table 4).

TABLE 4

| | | TMA Slides | | | |
|---|---|---|---|---|---|
| Pathology | | CO808-036 | CO809a-C051 | BC05002a-E068 | Total |
| Colon Cancer | N | 20 | 10 | 18 | 48 |
| | % | 34.48 | 17.54 | 45.0 | |
| Node Metastatis | N | 8 | 0 | 6 | 14 |
| | % | 13.79 | 0 | 15.0 | |
| Cancer Adjacent | N | 9 | 0 | 4 | 13 |
| | % | 15.52 | 0 | 10 | |
| Adenoma | N | 7 | 26 | 1 | 34 |
| | % | 12.07 | 45.61 | 2.5 | |
| Inflammation | N | 10 | 12 | 5 | 27 |
| | % | 17.24 | 21.05 | 12.5 | |
| Normal Mucosa | N | 4 | 9 | 6 | 19 |
| | % | 6.9 | 15.79 | 15.0 | |
| Total | | 58 | 57 | 40 | 155 |

Approximately half included unique colorectal cancer patients, which was divided into primary tumor (N=48), adjacent normal mucosa (N=12) and metastasized lymph nodes (N=14). The other half included benign lesions (22 adenoma and 17 inflammation) and normal mucosa without any colorectal pathologies (N=19). As reported in Table 3, each array showed the identical mean staining score after normalization. Compared with normal mucosa without any colorectal pathology, cancer adjacent mucosa had a statistically significantly higher mean normalized staining score (p=0.018), while primary tumors themselves exhibited a significantly lower mean score (P=0.013). Benign lesions and lymph nodes showed equivalent staining to normal mucosa (Table 5).

TABLE 5

| Pathology | N | Normalized Score Mean | Standard Error | P-value* |
|---|---|---|---|---|
| Colon Cancer | 48 | 1.372 | 0.125 | 0.0126 |
| Node Metastasis | 14 | 1.880 | 0.231 | 0.7853 |
| Cancer Adjacent | 13 | 2.719 | 0.240 | 0.0177 |
| Adenoma | 34 | 1.649 | 0.148 | 0.2070 |
| Inflammation | 27 | 1.988 | 0.166 | 0.9218 |
| Normal Mucosa | 19 | 1.963 | 0.198 | — |

*Difference from normal mucosa

Figure 2:
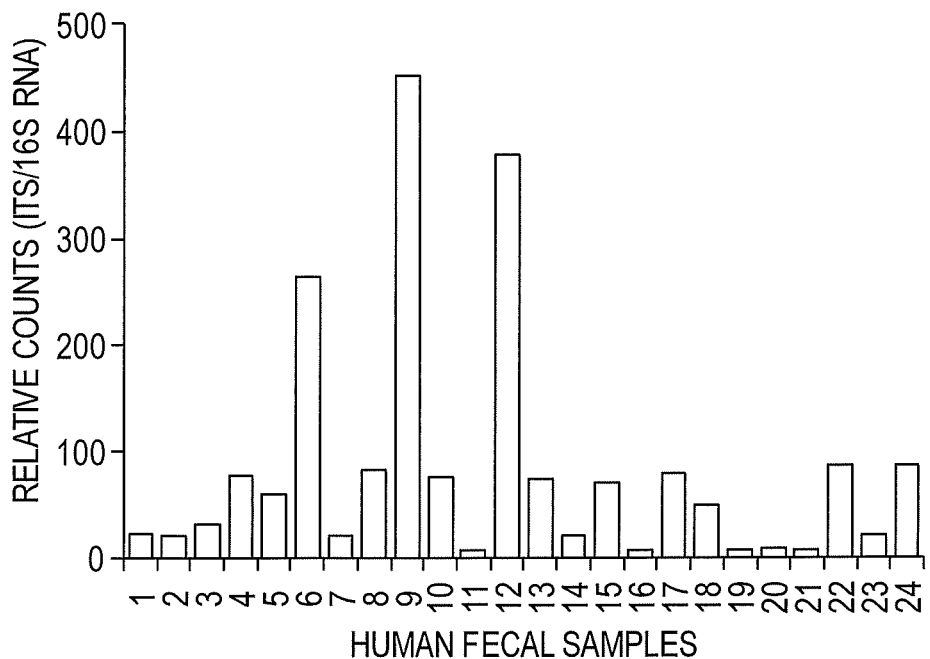
FIG. 2 shows amplification of *Salmonella* AvrA in human fecal samples. Human DNA samples (n=24) were amplified using real-time PCR. Primers for universal bacterial 16sRNA, *Salmonella* 16S-23S internal transcribed spacer (ITS), as well as *Salmonella* AvrA were used. With the exception samples 18, 21 and 24, all samples exhibited amplification of *Salmonella* AvrA.

Expression of AvrA Gene in Healthy Human Fecal Samples. Little variation in overall bacterial 16S RNA was observed amongst 24 human fecal samples. However, as shown in FIG. 2 relative *Salmonella* counts, assessed by ITS over universal bacterial 16S RNA, varied markedly from sample to sample. With the exception of samples 18, 21 and 24, all samples exhibited amplification for *Salmonella* AvrA. These data are consistent with a high prevalence of antibodies against *Salmonella* flagellin found in Metropolitan Detroit population (Kato, et al. (2013) *Nutr. Cancer* 65(2): 169-77).

In summary, the data presented in this example demonstrate the presence of *Salmonella* AvrA protein in colorectal mucosa from mice with experimental infection and human clinical specimens. In addition, it has been shown that anti-AvrA-antibody is detectable by ELISA in mouse serum post-*Salmonella* infection. Using IHC, the distribution of AvrA in *Salmonella*-infected mouse colon and in Salmonella-infected mice with colon cancer was demonstrated. Furthermore, the presence of AvrA protein in inflammatory bowel disease and colorectal tumor tissue in human clinical samples was established. Moreover, human fecal samples exhibited amplification of nucleic acids encoding *Salmonella* AvrA. As such, these data indicate a novel role of this bacterial protein in colon cancer and demonstrate that this protein and antibodies to the same are useful markers for identifying an enhanced risk of developing inflammatory bowel disease or colorectal cancer.

EXAMPLE 3

Wnt1 in Infection-Associated Colorectal Cancer

Deregulation of the Wnt/β-catenin signal transduction pathway has been implicated in the pathogenesis of inflammatory bowel diseases (IBD) and colorectal cancer (Kenny, et al. (2005) *BMC Cancer* 5:3; Stanczak, et al. (2011) *Pathol. Oncol. Res.* 17(4):955-63; You, et al. (2008) *Dig. Dis. Sci.* 53(4):1013-9). *Salmonella* infection is a major public health concern, and colonization in humans can be chronic and increase the risk of IBD and colorectal cancer (Gradel, et al. (2009) *Gastroenterology* 137(2):495-501; Kato, et al. (2013) *Nutr. Cancer* 65(2):169-77). It has been shown that *Salmonella* use various strategies to regulate Wnt signaling. The activation of Wnt/β-catenin by *Salmonella* infection is involved in cell proliferation, inflammation, apoptosis, trans-differentiation, and tumorigenesis (Sun, et al. (2004) *Am. J. Physiol. Gastrointest. Liver Physiol.* 287 (1):G220-7; Ye, et al. (2007) *Am. J. Pathol.* 171(3):882-92; Zhang, et al. (2012) *PLoS ONE* 7(4):e34942; Tahoun, et al. (2012) *Cell Host Microbe* 12(5):645-56; Lu, et al. (2012) *Am. J. Physiol. Gastrointest. Liver Physiol.* 303(10):G1113-25; Lu, et al. (2010) *PLoS ONE.* 5(5):e10505; Liu, et al. (2011) *Am. J. Physiol. Gastrointest. Liver Physiol.* 301(6): G992-G1003; Liu, et al. (2012) *Inflamm. Bowel Dis.* 18(3): 418-29; Lu, et al. (2014) *Oncogenesis* 3:e105).

Wnt1 is a Wnt family member that triggers the Wnt/β-catenin signaling cascade. Contradictory studies have shown overexpression or a lack of expression of Wnt1 in tumor tissue compared to normal colonic mucosa (Vider, et al. (1996) *Oncogene* 12(1):153-8; Jeong, et al. (2015) *PLoS ONE* 10(2):e0116533; Khor, et al. (2006) *Int. J. Colorectal Dis.* 21(4):291-300). These inconsistent studies suggest that Wnt1 expression is regulated by an unknown mechanism in these analyzed cases of colorectal cancer. However, the mechanism by which enteric bacteria regulate Wnt1 and how Wnt1 modulates the host response to pathogenic bacteria were not determined.

This example demonstrates the effects of *Salmonella* infection on Wnt1 repression in intestinal epithelial cells in vitro and in vivo. The data presented herein indicate that Wnt1 protein expression is decreased after *Salmonella* colonization and that Wnt1 is involved in protecting intestinal cells by blocking the invasion of pathogenic bacteria and suppressing inflammation. Furthermore, decreased *Salmonella* invasion is observed in cells in which Wnt1 expression is knocked down and pro-inflammatory cytokines are significantly upregulated in response to *Salmonella* infection in Wnt1-knockdown cells. Further, Wnt1 is down-regulated in colorectal cancer patients, and Wnt1 down-regulation correlated with colorectal cancer progression. As such, gut bacteria regulate Wnt1 expression and contribute to infection-associated colon cancer.

Figure 3:
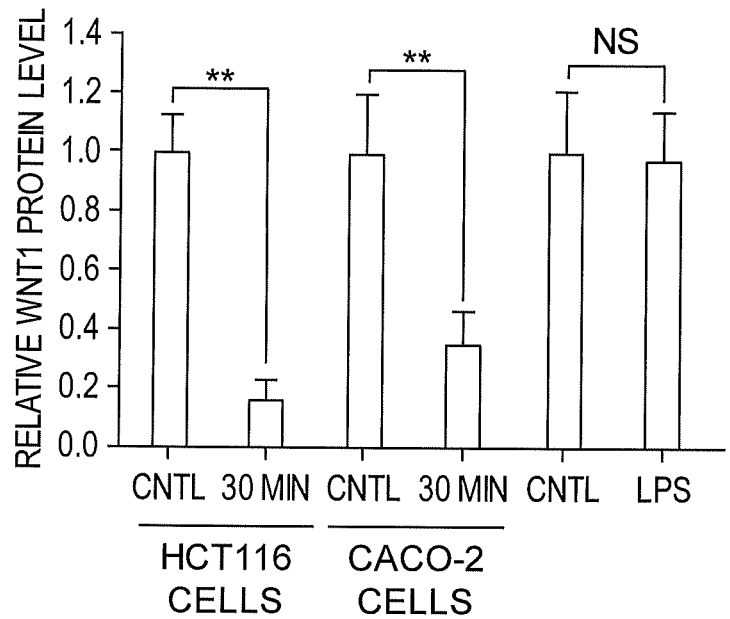
FIG. 3 shows that pathogenic *Salmonella* decreases Wnt1 protein expression in host cells. Human HCT116 or Caco-2 cells were incubated with wild-type *S. typhimurium* (SL 1314) for 30 minutes, washed, and incubated in fresh DMEM with 10% FBS for 30 minutes. Total cell lysates were analyzed for total Wnt1 levels by immunoblot. **P<0.05, n=3 separate experiments. "Cntl" indicates cells which were not treated with bacteria or LPS. NS=not significant.

Wnt1 Responds to *Salmonella* Infection. To determine whether Wnt1 protein plays a role in epithelial-*Salmonella* interactions, human intestinal epithelial HCT116 cells were infected with wild-type *Salmonella* Typhimurium strain SL 1314. It was found that *Salmonella* significantly decreased the total amount of Wnt1 protein in host cells after bacterial colonization for only 30 minutes (FIG. 3). The *Salmonella*-induced Wnt1 reduction lasted for more than 2 hour and occurred in a time-dependent manner. In human epithelial Caco-2 cells, *Salmonella* colonization also significantly decreased Wnt1 protein expression (FIG. 3). To determine whether the response was induced by lipopolysaccharide (LPS) from pathogenic bacteria, cells were treated with LPS. However, a similar change in Wnt1 expression was not observed, suggesting that the down-regulation of Wnt1 was specific to bacterial endotoxin.

To determine whether Wnt1 was reduced by regulation at the transcription level, Wnt1 mRNA expression was investigated in intestinal epithelial cells treated with *Salmonella*. However, RT-qPCR analysis showed that the Wnt1 mRNA level was not changed by *Salmonella* treatment in vitro. Overall, these data showed that pathogenic *Salmonella* reduces Wnt1 at the protein level but not the mRNA level.

Wnt1 is Regulated by *Salmonella* at the Post-Translational Level. Because Wnt1 protein destabilization occurred in the early stage of *Salmonella* invasion, it was posited that Wnt1 is regulated at the post-translational level upon *Salmonella* infection. Hence, it was determined whether *Salmonella* reduced Wnt1 protein through increased ubiquitination. To evaluate ubiquitination, Wnt1 was immunoprecipitated with anti-ubiquitin, anti-Wnt1 or anti-IgG (negative control) antibodies. Whereas Wnt1 was not immunoprecipitated by anti-IgG, the data indicated that *Salmonella* treatment induced more Wnt1 ubiquitination than did control treatment. Wnt1 ubiquitination was enhanced after *Salmonella* colonization for 30 minutes.

To determine whether Wnt1 level was reduced due to increased proteasomal degradation, cells were treated with the proteasome inhibitor MG132. In the presence of MG132, Wnt1 protein levels were stabilized after *Salmonella* infection to a level comparable to that of control cells without treatment. Taken together, these data indicated that increased ubiquitination and proteasomal degradation of Wnt1 occurs during *Salmonella* infection.

Wnt1 Protein is Directly Involved in *Salmonella*-Induced Inflammation. To further investigate the biological role of Wnt1 in *Salmonella*-induced inflammation, three separate CRISPR sgRNA sequences were designed to target the N-terminus of Wnt1 thereby generating truncating mutations. After puromycin selection, three clones were identified, and western blot analysis confirmed the heterozygous knockout status of these clones. The inflammatory response was subsequently assessed by evaluating the pro-inflammatory cytokines IL-8, IL-6 and GM-CSF in Wnt1-knockdown cells. Upon *Salmonella* colonization, the mRNA expression levels of IL-8, IL-6 and GM-CSF were significantly increased in Wnt1-knockdown cells compared to control HCT116 cells. Consistent with mRNA levels, ELISA assays showed that IL-6 production in culture supernatant was significantly increased in Wnt1-knockdown supernatant, compared to that of control group. However, no changes were observed for IL-8 and GM-CSF in Wnt1-knockdown supernatant. These data implicated that different cytokines may have different secretion times or are regulated differently.

Based upon the down-regulation Wnt1, it was further posited that overexpression of Wnt1 would not induce or induce less inflammation in response to *Salmonella* infection. However, contrary to this expectation, overexpression of Wnt1 inhibited the inflammary response similar to that of down-regulating Wnt1. As such, it was inferred that are coordination effects of different Wnts in response to bacterial infection. Previous results have demonstrated that overexpression of both Wnt2 and Wnt11 inhibits IL-8 production, and down-regulation of Wnt2 promotes IL-8 production (Liu, et al. (2011) *Am. J. Physiol. Gastrointest. Liver Physiol.* 301(6):G992-G1003; Liu, et al. (2012) *Inflamm. Bowel Dis.* 18(3):418-29). Therefore, expression of Wnt2 and Wnt11 was measured upon modulation of Wnt1. This analysis indicated that Wnt2 and Wnt11 were up-regulation in Wnt1 knockdown cells, whereas Wnt2 showed down-regulation when Wnt1 was overexpressed. Hence, these data indicated that the three Wnts may have varying effects in response to pathogenic bacterial infection and the reduction in Wnt1 levels may play a protective role in bacteria-induced intestinal inflammation.

Wnt1 Reduction Protects Cells from *Salmonella* Invasion. To study the physiological relevance of Wnt1 in Salmonella-host interactions, a green fluorescence-tagged *Salmonella* strain was used to detect bacterial invasion in human intestinal epithelial HCT116 cells. This analysis indicated that there were fewer green *Salmonella* cells that had invaded Wnt1-knockdown cells compared to wild-type cells. The number of *Salmonella* that invaded HCT116 cells with normal or reduced Wnt1 protein levels was counted and it was observed that Wnt1-knockdown epithelial cells had fewer internalized *Salmonella* than did control cells with basal Wnt1 expression. However, there was no difference in the number of cells with attached *Salmonella* between the control and Wnt1-knockdown groups. In the gain-of-functional study, overexpression of Wnt1 led to more internalized *Salmonella* than control cells. Regarding the attached Salmonella, there was no difference between the control and Wnt1-overexpression groups. Hence, these data indicated that Wnt1 regulated *Salmonella* invasion but not the attachment during the bacterial-intestinal epithelial cells interactions.

Figure 4:
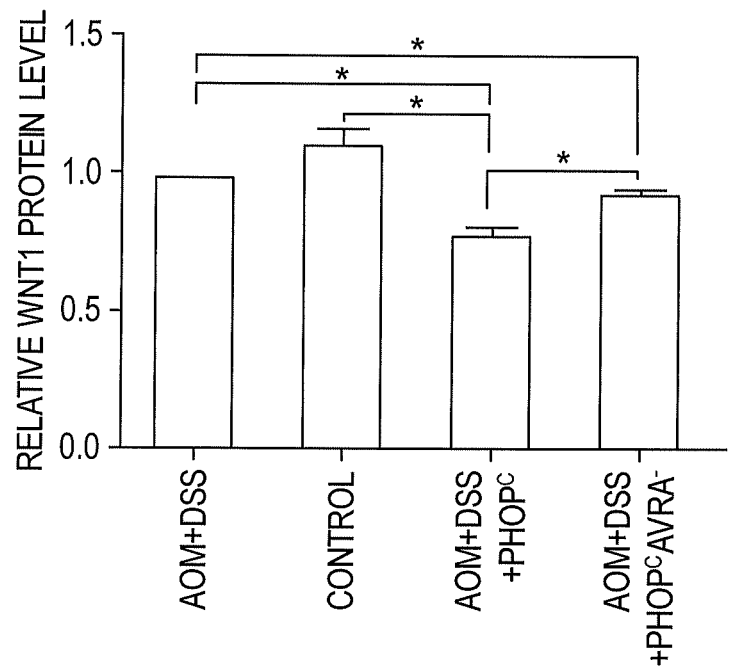
FIG. 4 shows that *Salmonella* effector AvrA regulates Wnt1 expression in *Salmonella*-infected intestine and infection-associated tumors. Mice were untreated (control) or treated with AOM+DSS and infected with *S. typhimurium* PhoP$^c$ or PhoP$^c$AvrA$^-$ (AvrA gene knockout). Wnt1 protein levels were assessed by western blot analysis 49 weeks post infection. *P<0.05

Down-Regulating Wnt1 Promotes Cancer Cell Invasion and Migration. Previous studies have reported the pathological changes associated with chronic *Salmonella* infection and differences in tumor development (Lu, et al. (2014) *Oncogenesis* 3:e105). Wnt ligands are involved in colon cancer development (Portiri, et al. (1997) *Oncogene* 15(23): 2833-9). Thus, the physiological relevance of Wnt1 in epithelial cells was assessed in a bacteria-infected mouse model and an infection-associated colon cancer model. AvrA is a *Salmonella* effector protein known to activate the Wnt signaling pathway (Liu, et al. (2011) *Am. J. Physiol. Gastrointest. Liver Physiol.* 301(6):G992-G1003; Liu, et al. (2012) *Inflamm. Bowel Dis.* 18(3):418-29). It was observed that Wnt1 expression levels were down-regulated by AvrA-expressing *Salmonella* but stabilized by AvrA-deficient *Salmonella* in the intestine of *Salmonella*-infected mice. Further, Wnt1 protein levels decreased significantly in tumors of mice infected with the AvrA-sufficient *Salmonella* strain (PhoP$^c$) and increased significantly in tumors from mice infected with the AvrA-deficient *Salmonella* strain PhoP-$^c$AvrA$^-$ (FIG. 4). However, Wnt1 protein levels did not change significantly in tumors after AOM-DSS treatment and were similar to that of the control group. Wnt1 distribution in colon of mice with or without tumor was confirmed by immunostaining. Whereas Wnt1 was reduced in tumors and adjacent "normal" mucosa in AvrA-sufficient *Salmonella* PhoP$^c$, β-catenin was enhanced in the tumors. Activated β-catenin was also found to be translocated into the nucleus of adjacent "normal" mucosa. Taken together, these results indicate that Wnt protein levels are lower in colon from mice infected with AvrA-expressing bacteria than in those treated with AOM/DSS alone or colonized with AvrA-deficient *Salmonella*.

Wnt1 protein in the colorectal tumor tissue was subsequently examined in four human clinical samples. All four colorectal samples showed high-to-moderate differentiated adenocarcinoma. In addition, Wnt1 protein levels were dramatically decreased in the differentiated adenocarcinoma tissues, compared to para-carcinoma tissue. Taken together, these data indicate that Wnt1 is involved in the colon cancer development.

Figure 5:
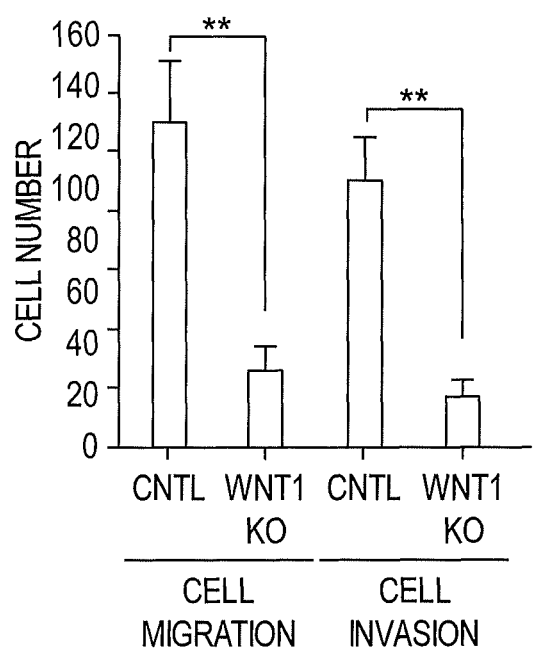
FIG. 5 shows the role of Wnt1 down-regulation in cancer development. Control (Cntl) and Wnt1 knockout (Wnt1 KO) cells were allowed to migrate for 24 hours in chambers (Cell Migration) or for 48 hours in chambers were coated with a solubilized basement membrane preparation sold under the trademark MATRIGEL® (Cell Invasion). The mean±SD is from 3 replicate experiments. **P<0.05.

To detect the role of knockdown of Wnt1 in the colon cancer development, cell migration and invasion were examined. This analysis indicated that the migration and invasion abilities of HCT116 cells with Wnt1 knockdown were dramatically decreased compared with controls (FIG. 5). Further, the proliferation-, migration- and invasion-related genes, c-myc, FlnA, TIMP3 and Nm23 were down-regulated in Wnt1 knockdown cells, compared to control cells indicating that Wnt1 participated in the development of colorectal cancer.

This study demonstrated that *Salmonella* infection reduces Wnt1 protein expression in intestinal epithelial cells both in vitro and in vivo. Further, down-regulation of Wnt1 expression increases the expression of inflammation cytokines, including IL-8, GM-CSF, and IL-6, in response to *Salmonella* infection and inhibits *Salmonella* invasion. Moreover, Wnt1 protein levels were reduced in the colorectal mucosa of bacteria-infected mice, wherein said reduction promoted cancer cell migration and invasion. As such, Wnt1 is directly involved in regulating intestinal inflammation and cancer development induced by enteric bacteria. Therefore, these data demonstrate the use of Wnt1 as a useful marker for diagnosing colorectal cancer and as a target for the treatment of colorectal cancer in a subject having a previous *Salmonella* infection.

EXAMPLE 4

*Salmonella* Enteritidis AvrA Suppresses Autophagy by Targeting Beclin-1 Protein

*Salmonella* possesses a range of effector proteins that are translocated into the host cells via a type III secretion system (T3SS). These effector proteins are generally assumed to influence the host's cellular functions to facilitate *Salmonella* invasion and intracellular carriage. AvrA is one of the *Salmonella* effectors secreted by the *Salmonella* pathogenicity island 1 (SPI-1) T3SS. The AvrA protein in *Salmonella* Typhimurium is an anti-inflammatory effector that possesses acetyltransferase activity and inhibits the host c-Jun N-terminal kinase (JNK)/AP-1 and NF-κB signaling pathways. Through these methods, AvrA inhibits the host inflammatory response and stabilizes the intestinal tight junctions to the benefit of *Salmonella* survival.

Using wild-type, *Salmonella* Enteritidis C50336, S.E-AvrA$^-$ and S.E-AvrA$^-$/pAvrA$^+$ (S.E-AvrA$^+$), this example provides data demonstrating that *Salmonella* Enteritidis AvrA inhibits the autophagic response by decreasing Beclin-1 expression. In cell cultures, organoids and infected mice, the physiologically related effects and molecular mechanism of AvrA regulation of autophagy in intestinal epithelial cells was explored.

*Salmonella* Enteritidis AvrA Decreases Autophagy Markers and Enhanced Bacterial Invasion in vitro. Autophagy is an important cell-autonomous defense mechanism required for pathogen clearance. LC3 and p62 are well-recognized markers for autophagic activity. In this study, it was found that in human intestinal epithelial HCT116 cells, the conversion of LC3 I into LC3 II was increased after S.E-AvrA$^-$ infection compared to that after wild-type S.E or S.E-AvrA$^+$ infection. Notably, p62, which is a bona fide target of autophagosomal degradation, was decreased in the cells infected with the S.E-AvrA mutant strain compared with the expression in cells infected with the S.E-wild type or S.E-AvrA$^+$ strains. A densitometry analysis showed a significant difference between the cells infected with the different S.E strains. Meanwhile, HCT116 cells pre-treated with fluorescent reagent sold under the trademark LYSOTRACKER® showed more lysosomes in the cells infected with the S.E-AvrA mutant strain than in the cells infected with the AvrA expressed strains. The role of AvrA in *Salmonella* Enteritidis invasion is unknown. Thus, the invasion ability of the *Salmonella* Enteritidis strain with AvrA expression was compared to that without AvrA expression. It was observed that S.E-AvrA$^-$-colonized human epithelial cells showed a decreased intracellular bacterial load compared to those colonized with wild-type S.E or S.E-AvrA$^+$. Similar trends in autophagic activity following S.E-AvrA$^-$, S.E-AvrA$^+$ and S.E-wild-type infection were noted in human Caco-2 BBE and SKCO-15 cells. Taken together, these data indicate that the *Salmonella* Enteritidis effector AvrA inhibits autophagy in vitro.

AvrA Interacts with Beclin-1 and Reduces Beclin-1 at the Protein Level. Beclin-1, a key molecular regulator of autophagy, interacts with several cofactors to regulate the lipid kinase Vps-34 protein and promote the formation of Beclin-1-Vps34-Vps15 core complexes, thereby inducing autophagy. Thus, it was determined whether the protein level of Beclin-1 was changed by the infection with the different S.E strains. This analysis indicated that Beclin-protein expression was significantly decreased after colonization by strains expressing AvrA for 1 hour. In contrast, the cells colonized with the S.E-AvrA$^-$ bacteria maintained Beclin-1 protein expression. The interaction of AvrA/Beclin-1 in the HCT116 cells was further assessed by immunoprecipitation. Vps34 was used as a positive control. This analysis indicated that exogenous AvrA (c-myc-tag) co-immunoprecipitated with exogenous Beclin-1 (HA-tag), indicating that AvrA interacted with Beclin-1. To verify that AvrA affects the protein expression of Beclin-1, plasmids harboring nucleic acids encoding wild-type AvrA or an AvrA C186A mutant (mutated at the key cysteine required for AvrA activity (Ye, et al. (2007) *Am. J. Pathol* 171:882-892)) were transfected into HCT116 cells. As expected, wild-type AvrA decreased endogenous Beclin-1 protein expression. However, the AvrA C186A mutant maintained endogenous Beclin-1 protein expression. Therefore, the data indicate that the S.E effector AvrA physically binds with Beclin-1 and changes its protein levels to inhibit autophagy.

AvrA Inhibits the JNK Signaling Pathway to Decrease Beclin-1. Beclin-1 is regulated by the JNK signaling pathway. Previous studies have shown that *Salmonella* AvrA inhibits the activation of the JNK signaling pathways (Jones, et al. (2008) *Cell Host Microbe* 3:233-244; Lin, et al. (2016) *J. Biol. Chem.* 291:26837-26849). Using western blot analysis, it was found that the protein levels of p-JNK and p-c-Jun were higher in the S.E-AvrA$^-$-infected cells than in the cells infected by the S.E-wild-type or S.E-AvrA$^+$ strains. Meanwhile, a luciferase reporter assay showed that AP-1 transcription was increased, as a consequence of the activation of JNK/c-JUN. These data indicate that the JNK/c-jun pathway and AP-1 transcription are more highly activated in the S.E-AvrA⁻-infected cells than in the cells infected with the AvrA present strains. Interestingly, after treatment with the JNK inhibitor SP600125, the level of Beclin-1 and P62 protein expression was not different between the cells infected with AvrA or without AvrA, indicating that the AvrA-related responses were abolished by the JNK inhibitor. These data indicate that the S.E effector AvrA inhibits the autophagic response by decreasing Beclin-1, and it occurs by inhibiting the JNK/c-Jun/AP-1 signaling pathways.

AvrA C186A mutant Abolishes Regulation of Exogenous Beclin-1. To further study the function of the AvrA protein, plasmids harboring nucleic acids encoding a wild-type AvrA or an AvrA C186A mutant were cotransfected with a plasmid encoding wild-type Beclin-1. The AvrA C186A mutation is known to abolish the enzyme activity of AvrA. These data showed that wild-type AvrA decreased not only the endogenous Beclin-1 protein but also the exogenous Beclin-1 protein. In contrast, the C186A mutant of AvrA abolished the regulation of AvrA on Beclin-1 expression. Moreover, the protein levels of p-JNK, p-c-Jun and Beclin-1 were decreased in the wild-type AvrA transfected cells compared with the cells transfected with the AvrA C186A mutant. These data verified that AvrA decreased Beclin-1 by inhibiting the JNK signaling pathways, whereas the AvrA C186A mutation abolished its regulation.

Previous analysis indicated that AvrA is also a deubiquitinase that regulates target proteins (Ye, et al. (2007) *Am. J. Pathol* 171:882-892). Thus, a possible mechanism of the effect of AvrA on Beclin-1 at the ubiquitination level was investigated. Cells were cotransfected with plasmids harboring nucleic acids encoding a wild-type AvrA or an AvrA C186A mutant and a plasmid encoding wild-type Beclin-1 followed by the addition of the proteasome inhibitor MG262 to prevent the proteasomal degradation of ubiquitinated proteins. When the cells were cotransfected with wild-type AvrA and wild-type Beclin-1, decreased levels of ubiquitinated Beclin-1 were observed; whereas Beclin-1 ubiquitination increased in the cells cotransfected with the AvrA C186A mutant and wild-type Beclin-1.

AvrA Expressing Bacteria Reduce the Level of Beclin-1 in Mouse Organoids. Intestinal organoid culture is an established 3D system to determine the bacterial-epithelial interactions post *Salmonella* infection (Zhang, et al. (2014) *Physiological reports* 2:e12147). Upon infection with S.E-wild-type expressing AvrA, Beclin-1 protein expression was significantly decreased in the intestinal organoid culture. In contrast, the organoids colonized with the S.E-AvrA⁻ mutant strain exhibited an increase in Beclin-1 protein expression, whereas S.E-AvrA⁺ reduced Beclin-1 expression. Moreover, AvrA-associated changes of P62, LC3 II/LC3 I, and p-JNK in the *Salmonella*-infected organoids were observed. Decreased autophagy marker P62 was further confirmed in organoids colonized with the S.E-AvrA⁻ strain in comparison with organoids infected by the S.E-wild-type and S.E-AvrA⁺ strains by immunostaining. These changes in the 3D organoids were consistent with AvrA-suppressed autophagy observed in the 2D cultured cell lines.

AvrA Changes the Levels of Beclin-1 and Affects the Function of Paneth cell Granules of Ileal Tissue in Mice. To study the role of the S.E effector AvrA in an in vivo model of natural intestinal infection, the streptomycin pretreatment mouse model of enteric salmonellosis was used (Barthel, et al. (2003) *Infect. Immun.* 71:2839-2858; Vijay-Kumar, et al. (2006) *Am. J. Pathol.* 169:1686-1700). C57BL/6 mice (female, 6-8 weeks) were pretreated with streptomycin for 24 hours before infection with the S.E-wild-type, S.E-AvrA⁻ or S.E-AvrA⁺ strains by oral gavage. In the ileum samples from the S.E-wild-type-infected mice, Beclin-1 protein expression was significantly decreased compared to the expression in the samples from the S.E-AvrA⁻-infected mice. As expected, decreased P62, increased conversion of LC3 I into LC3 II and activation of the JNK pathway were also found in mice infected with the S.E-AvrA⁻ strain compared with those in the mice infected by the S.E-wild-type strain. These data suggest that AvrA inhibits the JNK signaling pathway to decrease Beclin-1 expression and impair the autophagic response in vivo.

Deficits in the autophagy pathway impair Paneth cell function in intestine. Thus, the number of Paneth cells were counted using a previously reported method to stain lysozymes (Wu, et al. (2015) *Gut* 64:1082-1094; Cadwell, et al. (2008) *Nature* 456:259-263). The abnormal Paneth cells were grouped as D1 (disordered), D2 (depleted), or D3 (diffuse). Fewer normal Paneth cells (D0) were found in mice infected with the S.E-wild-type strain than in mice infected with the S.E-AvrA⁻ strain. Consequently, the number of abnormal Paneth cells (D1-D3) increased in the mice infected with the wild-type S.E strain.

S.E-AvrA⁻ Colonized Paneth Cells Secrete High Levels of TNF-α. Using a modified method of Paneth cell purification, a paneth cell population having a purity of over 95% was obtained. Immunofluorescence staining of lysozyme was carried out to further evaluate the purified Paneth cells. About 95% purified Paneth cells showed strong positive staining of lysozyme, which is consistent with the purity of Paneth cells after sorting detected by flow cytometry. Lysozyme staining was primarily located in the cytoplasmic around the nucleus. It was posited that the absence of AvrA may be associated with changes in cytokines in Paneth cells after S.E colonization. Thus, expression of a range of pro-inflammatory cytokines and other cytokines including TNF-α, IL-13, IL-17F, IL-22, MCP-1, IL-21, IFN-γ, IL-1β, IL-6, IL-17A were assessed by qPCR to evaluate the secretory features of background cytokines in Paneth cells. Among the ten cytokines, TNF-α was significantly lower in the Paneth cells infected with the S.E-AvrA⁻ bacteria compared with the cells infected with the strains containing AvrA. But IL-13 was significantly higher in the Paneth cells infected with the S.E-AvrA⁻ bacteria compared with the cells infected with strains containing AvrA.

Taken together, the in vitro and in vivo data revealed a new mechanism by which AvrA in *S. Enteritidis* reduces Beclin-1 protein expression, thus attenuating the autophagic response in intestinal epithelial cells. This study provides insights into a newly identified strategy by which a bacterial effector targeting host proteins to suppress autophagy.

What is claimed is:

1. A kit comprising:

(A) at least one of:

(i) a set of fluorescently labeled primers having the nucleotide sequences of

GAATGGAAGGCGTTGAATCTGC (SEQ ID NO:5)

and

GTTGTGCGCCTTGAGTATGTTTGTAA (SEQ ID NO:6); or (ii) a multiwell plate, wherein wells of the multiwell plate are coated with purified AvrA protein; and (B) a set of fluorescently labeled primers having the nucleotide sequences of

GAGCCACGAGTTTGGATGTT (SEQ ID NO:14)

and

TGAGGAGAGAAGAGGGACCA. (SEQ ID NO:15)

* * * * *

SEQUENCE LISTING

<160> NUMBER OF SEQ ID NOS: 32

<210> SEQ ID NO 1
<211> LENGTH: 19
<212> TYPE: DNA

<213> ORGANISM: Homo sapiens

<400> SEQUENCE: 1
tcctacggga ggcagcagt                                                19

<210> SEQ ID NO 2
<211> LENGTH: 26
<212> TYPE: DNA
<213> ORGANISM: Homo sapiens

<400> SEQUENCE: 2
ggactaccag ggtatctaat cctgtt                                        26

<210> SEQ ID NO 3
<211> LENGTH: 24
<212> TYPE: DNA
<213> ORGANISM: Homo sapiens

<400> SEQUENCE: 3
tatgccccat cgtgtagtca gaac                                          24

<210> SEQ ID NO 4
<211> LENGTH: 20
<212> TYPE: DNA
<213> ORGANISM: Homo sapiens

<400> SEQUENCE: 4
tgcggctgga tcacctcctt                                               20

<210> SEQ ID NO 5
<211> LENGTH: 22
<212> TYPE: DNA
<213> ORGANISM: Homo sapiens

<400> SEQUENCE: 5
gaatggaagg cgttgaatct gc                                            22

<210> SEQ ID NO 6
<211> LENGTH: 26
<212> TYPE: DNA
<213> ORGANISM: Homo sapiens

<400> SEQUENCE: 6
gttgtgcgcc ttgagtatgt ttgtaa                                        26

<210> SEQ ID NO 7
<211> LENGTH: 20
<212> TYPE: DNA
<213> ORGANISM: Homo sapiens

<400> SEQUENCE: 7
tgctacgctg ctgctggcgc                                               20

<210> SEQ ID NO 8
<211> LENGTH: 20
<212> TYPE: DNA
<213> ORGANISM: Homo sapiens

<400> SEQUENCE: 8
ggcagttccg gaatctcctc                                               20

<210> SEQ ID NO 9
<211> LENGTH: 20

```
<212> TYPE: DNA
<213> ORGANISM: Homo sapiens

<400> SEQUENCE: 9
gacagttcca gcggcgattc                                           20

<210> SEQ ID NO 10
<211> LENGTH: 28
<212> TYPE: DNA
<213> ORGANISM: Homo sapiens

<400> SEQUENCE: 10
cggaattcat ggggctctgg gcgctgtt                                  28

<210> SEQ ID NO 11
<211> LENGTH: 28
<212> TYPE: DNA
<213> ORGANISM: Homo sapiens

<400> SEQUENCE: 11
gctctagaca gacactcgtg cagtacgc                                  28

<210> SEQ ID NO 12
<211> LENGTH: 20
<212> TYPE: DNA
<213> ORGANISM: Homo sapiens

<400> SEQUENCE: 12
agagcaagag aggcatcctc                                           20

<210> SEQ ID NO 13
<211> LENGTH: 19
<212> TYPE: DNA
<213> ORGANISM: Homo sapiens

<400> SEQUENCE: 13
gacggccgca tcttcttgt                                            19

<210> SEQ ID NO 14
<211> LENGTH: 20
<212> TYPE: DNA
<213> ORGANISM: Homo sapiens

<400> SEQUENCE: 14
gagccacgag tttggatgtt                                           20

<210> SEQ ID NO 15
<211> LENGTH: 20
<212> TYPE: DNA
<213> ORGANISM: Homo sapiens

<400> SEQUENCE: 15
tgaggagaga agagggacca                                           20

<210> SEQ ID NO 16
<211> LENGTH: 24
<212> TYPE: DNA
<213> ORGANISM: Homo sapiens

<400> SEQUENCE: 16
tgcataaaga catactccaa acct                                      24

<210> SEQ ID NO 17
```

```
<211> LENGTH: 22
<212> TYPE: DNA
<213> ORGANISM: Homo sapiens

<400> SEQUENCE: 17
aattctcagc cctcttcaaa aa                                          22

<210> SEQ ID NO 18
<211> LENGTH: 21
<212> TYPE: DNA
<213> ORGANISM: Homo sapiens

<400> SEQUENCE: 18
agtggctgca ggacatgaca a                                           21

<210> SEQ ID NO 19
<211> LENGTH: 21
<212> TYPE: DNA
<213> ORGANISM: Homo sapiens

<400> SEQUENCE: 19
caatctgagg tgcccatgct a                                           21

<210> SEQ ID NO 20
<211> LENGTH: 20
<212> TYPE: DNA
<213> ORGANISM: Homo sapiens

<400> SEQUENCE: 20
ggcgtctcct gaacctgagt                                             20

<210> SEQ ID NO 21
<211> LENGTH: 20
<212> TYPE: DNA
<213> ORGANISM: Homo sapiens

<400> SEQUENCE: 21
ggggatgaca agcagaaagt                                             20

<210> SEQ ID NO 22
<211> LENGTH: 20
<212> TYPE: DNA
<213> ORGANISM: Homo sapiens

<400> SEQUENCE: 22
tcccagcgca aggggctgaa                                             20

<210> SEQ ID NO 23
<211> LENGTH: 21
<212> TYPE: DNA
<213> ORGANISM: Homo sapiens

<400> SEQUENCE: 23
gccggatgca ggcgtagtgt t                                           21

<210> SEQ ID NO 24
<211> LENGTH: 25
<212> TYPE: DNA
<213> ORGANISM: Homo sapiens

<400> SEQUENCE: 24
acctgaagga ccgtccattc tttgc                                       25
```

```
<210> SEQ ID NO 25
<211> LENGTH: 23
<212> TYPE: DNA
<213> ORGANISM: Homo sapiens

<400> SEQUENCE: 25
gtgaaaccac aagccgatct cct                                          23

<210> SEQ ID NO 26
<211> LENGTH: 20
<212> TYPE: DNA
<213> ORGANISM: Homo sapiens

<400> SEQUENCE: 26
tcaagaggcg aacacacaac                                              20

<210> SEQ ID NO 27
<211> LENGTH: 20
<212> TYPE: DNA
<213> ORGANISM: Homo sapiens

<400> SEQUENCE: 27
ggccttttca ttgttttcca                                              20

<210> SEQ ID NO 28
<211> LENGTH: 20
<212> TYPE: DNA
<213> ORGANISM: Homo sapiens

<400> SEQUENCE: 28
gccagaagag cagcttcaca                                              20

<210> SEQ ID NO 29
<211> LENGTH: 20
<212> TYPE: DNA
<213> ORGANISM: Homo sapiens

<400> SEQUENCE: 29
ccttgagcag gtaggacacg                                              20

<210> SEQ ID NO 30
<211> LENGTH: 15
<212> TYPE: PRT
<213> ORGANISM: Homo sapiens

<400> SEQUENCE: 30

Cys Gly Glu Glu Pro Phe Leu Pro Ser Asp Lys Ala Asp Arg Tyr
1               5                   10                  15

<210> SEQ ID NO 31
<211> LENGTH: 302
<212> TYPE: PRT
<213> ORGANISM: Homo sapiens

<400> SEQUENCE: 31

Met Ile Phe Ser Val Gln Glu Leu Ser Cys Gly Gly Lys Ser Met Leu
1               5                   10                  15

Ser Pro Thr Thr Arg Asn Met Gly Ala Ser Leu Ser Pro Gln Pro Asp
            20                  25                  30

Val Ser Gly Glu Leu Asn Thr Glu Ala Leu Thr Cys Ile Val Glu Arg
        35                  40                  45

Leu Glu Ser Glu Ile Ile Asp Gly Ser Trp Ile His Ile Ser Tyr Glu
    50                  55                  60
```

Glu Thr Asp Leu Glu Met Met Pro Phe Leu Val Ala Gln Ala Asn Lys
65                  70                  75                  80

Lys Tyr Pro Glu Leu Asn Leu Lys Phe Val Met Ser Val His Glu Leu
                85                  90                  95

Val Ser Ser Ile Lys Glu Thr Arg Met Glu Gly Val Glu Ser Ala Arg
            100                 105                 110

Phe Leu Val Asn Met Gly Ser Ser Gly Ile His Ile Ser Val Val Asp
            115                 120                 125

Phe Arg Val Met Asp Gly Lys Thr Ser Val Ile Leu Phe Glu Pro Ala
            130                 135                 140

Ala Cys Ser Ala Phe Gly Pro Ala Leu Leu Ala Leu Arg Thr Lys Ala
145                 150                 155                 160

Ala Leu Glu Arg Glu Gln Leu Pro Asp Cys Tyr Phe Ala Met Val Glu
                165                 170                 175

Leu Asp Ile Gln Arg Ser Ser Ser Glu Cys Gly Ile Phe Ser Leu Ala
            180                 185                 190

Leu Ala Lys Lys Leu Gln Leu Glu Phe Met Asn Leu Val Lys Ile His
            195                 200                 205

Glu Asp Asn Ile Cys Glu Arg Leu Cys Gly Glu Pro Phe Leu Pro
210                 215                 220

Ser Asp Lys Ala Asp Arg Tyr Leu Pro Val Ser Phe Tyr Lys His Thr
225                 230                 235                 240

Gln Gly Ala Gln Arg Leu Asn Glu Tyr Val Glu Ala Asn Pro Ala Ala
                245                 250                 255

Gly Ser Ser Ile Val Asn Lys Lys Asn Glu Thr Leu Tyr Glu Arg Phe
            260                 265                 270

Asp Asn Asn Ala Val Met Leu Asn Asp Lys Lys Leu Ser Ile Ser Ala
            275                 280                 285

His Lys Lys Arg Ile Ala Glu Tyr Lys Ser Leu Leu Lys Pro
    290                 295                 300

<210> SEQ ID NO 32
<211> LENGTH: 370
<212> TYPE: PRT
<213> ORGANISM: Homo sapiens

<400> SEQUENCE: 32

Met Gly Leu Trp Ala Leu Leu Pro Gly Trp Val Ser Ala Thr Leu Leu
1               5                   10                  15

Leu Ala Leu Ala Ala Leu Pro Ala Ala Leu Ala Ala Asn Ser Ser Gly
                20                  25                  30

Arg Trp Trp Gly Ile Val Asn Val Ala Ser Ser Thr Asn Leu Leu Thr
            35                  40                  45

Asp Ser Lys Ser Leu Gln Leu Val Leu Glu Pro Ser Leu Gln Leu Leu
50                  55                  60

Ser Arg Lys Gln Arg Arg Leu Ile Arg Gln Asn Pro Gly Ile Leu His
65                  70                  75                  80

Ser Val Ser Gly Gly Leu Gln Ser Ala Val Arg Glu Cys Lys Trp Gln
                85                  90                  95

Phe Arg Asn Arg Arg Trp Asn Cys Pro Thr Ala Pro Gly Pro His Leu
            100                 105                 110

Phe Gly Lys Ile Val Asn Arg Gly Cys Arg Glu Thr Ala Phe Ile Phe
            115                 120                 125

Ala Ile Thr Ser Ala Gly Val Thr His Ser Val Ala Arg Ser Cys Ser

-continued

```
                130                 135                 140
Glu Gly Ser Ile Glu Ser Cys Thr Cys Asp Tyr Arg Arg Arg Gly Pro
145                 150                 155                 160

Gly Gly Pro Asp Trp His Trp Gly Gly Cys Ser Asp Asn Ile Asp Phe
                165                 170                 175

Gly Arg Leu Phe Gly Arg Glu Phe Val Asp Ser Gly Glu Lys Gly Arg
                180                 185                 190

Asp Leu Arg Phe Leu Met Asn Leu His Asn Asn Glu Ala Gly Arg Thr
                195                 200                 205

Thr Val Phe Ser Glu Met Arg Gln Glu Cys Lys Cys His Gly Met Ser
                210                 215                 220

Gly Ser Cys Thr Val Arg Thr Cys Trp Met Arg Leu Pro Thr Leu Arg
225                 230                 235                 240

Ala Val Gly Asp Val Leu Arg Asp Arg Phe Asp Gly Ala Ser Arg Val
                245                 250                 255

Leu Tyr Gly Asn Arg Gly Ser Asn Arg Ala Ser Arg Ala Glu Leu Leu
                260                 265                 270

Arg Leu Glu Pro Glu Asp Pro Ala His Lys Pro Pro Ser Pro His Asp
                275                 280                 285

Leu Val Tyr Phe Glu Lys Ser Pro Asn Phe Cys Thr Tyr Ser Gly Arg
                290                 295                 300

Leu Gly Thr Ala Gly Thr Ala Gly Arg Ala Cys Asn Ser Ser Ser Pro
305                 310                 315                 320

Ala Leu Asp Gly Cys Glu Leu Leu Cys Cys Gly Arg Gly His Arg Thr
                325                 330                 335

Arg Thr Gln Arg Val Thr Glu Arg Cys Asn Cys Thr Phe His Trp Cys
                340                 345                 350

Cys His Val Ser Cys Arg Asn Cys Thr His Thr Arg Val Leu His Glu
                355                 360                 365

Cys Leu
    370
```